(12) United States Patent
Park et al.

(10) Patent No.: US 7,467,012 B1
(45) Date of Patent: Dec. 16, 2008

(54) RESPIRATION PARAMETERS CONTROLLED BY HEART RATE

(75) Inventors: Euljoon Park, Valencia, CA (US); Gene A. Bornzin, Simi Valley, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 348 days.

(21) Appl. No.: 11/166,617

(22) Filed: Jun. 24, 2005

(51) Int. Cl.
*A61N 1/05* (2006.01)
*A61B 5/08* (2006.01)

(52) U.S. Cl. .................. 607/20; 600/529; 600/484; 600/483; 600/526

(58) Field of Classification Search .............. 600/529, 600/513, 483, 484, 526; 607/20
See application file for complete search history.

(56) References Cited

U.S. PATENT DOCUMENTS

| | | | |
|---|---|---|---|
| 5,273,034 A | * 12/1993 | Nilsson | 607/18 |
| 5,800,467 A | 9/1998 | Park et al. | 607/17 |
| 5,814,086 A | * 9/1998 | Hirschberg et al. | 607/14 |
| 6,126,611 A | * 10/2000 | Bourgeois et al. | 600/529 |
| 6,415,183 B1 | * 7/2002 | Scheiner et al. | 607/42 |
| 6,572,557 B2 | * 6/2003 | Tchou et al. | 600/483 |
| 2005/0043644 A1 | * 2/2005 | Stahmann et al. | 600/529 |

FOREIGN PATENT DOCUMENTS

| | | |
|---|---|---|
| EP | 0940155 A2 | 9/1999 |
| EP | 0940155 A3 | 9/1999 |
| WO | WO 00/01438 | 1/2000 |
| WO | WO 01/41868 A1 | 6/2001 |

* cited by examiner

*Primary Examiner*—Carl H Layno
*Assistant Examiner*—Natasha N Patel

(57) ABSTRACT

Heart rate information is used at least in part to obtain one or more parameters for inducing respiration. In various implementations, respiratory parameters, such as a target breathing rate or a target tidal volume may be delivered by an implantable device to a patient during periods of altered respiration, such as sleep apnea or exercise. A respiratory parameter may also be obtained from a physiological variable, a patient's physical activity level, or metabolic demands.

16 Claims, 17 Drawing Sheets

RESPIRATION PARAMETERS CONTROLLED BY HEART RATE

TECHNICAL FIELD

The present subject matter relates generally to implantable cardiac devices, and more particularly, to controlling respiration parameters based on heart rate.

BACKGROUND

Early conventional cardiac pacing techniques sought to calculate a target heart rate based on metabolic demand. These techniques included measuring a patient's respiration rate or "breathing rate" as a measure of metabolic demand and selecting a heart rate that corresponded in some way to this breathing rate. The breathing rate was thought to correspond to oxygen consumption ($VO_2$), which in turn was known to be a fairly accurate indicator of metabolic demand, that is, absolute work intensity. Within a very narrow range, individuals exercising at the same intensity have the same $VO_2$, or need for oxygen. Using an assumption that breathing rate is a good measure of $VO_2$, conventional cardiac pacing devices were designed to increase the heart rate in response to an increased breathing rate.

A simple relationship of linear proportionality between heart rate and breathing rate adopted in conventional pacemakers is not very effective in several important circumstances. During sleep apnea (a common occurrence for many heart failure patients) and during exercise, more sophisticated techniques are needed to effectively establish a link between a given heart rate and a complementary breathing rate.

In general, while a person's breathing rate is roughly a derivative indicator of oxygen consumption, a much better indicator is minute ventilation (MV). A patient may increase oxygen intake not only by increasing the breathing rate, but even more so by changing tidal volume, i.e., the volume of air inspired with each breath. MV is a better measure of $VO_2$ than the breathing rate alone because MV is the product of the breathing rate times the tidal volume of each breath, that is, the volume of air inspired over a period of time, usually one minute. At rest, an average adult MV is about 6 liters of air per minute (air is approximately 20% oxygen), corresponding to the oxidation of enough fuel to provide the work intensity expected in an average adult at rest.

The tidal volume component of MV is also dependent on two other "ventilations," alveolar ventilation (VA) and dead space ventilation (VD). VA is the volume of air inspired per minute that reaches the alveoli and takes part in gas exchange (transfer of oxygen and carbon dioxide across the pulmonary capillaries). VD represents a volume of air that reaches the lungs but does not take part in gas exchange and is not considered part of VA.

During exercise, working muscles can increase their oxygen consumption immensely: for some muscles, up to one hundred times their resting rate of oxygen consumption. Averaged over the entire body, oxygen consumption can increase 20-25 times from the resting rate. The need for oxygen increases as the intensity of the exercise increases because aerobic pathways for producing energy must increasingly be used over anaerobic pathways.

As exercise increases, a person's breathing rate increases from approximately six to approximately twelve breaths per minute to a maximum of approximately sixty breaths per minute. Furthermore, the tidal volume can increase from approximately 0.5 liters per breath to approximately 2-3 liters per breath. These dramatic increases are responsible for a twenty to twenty-five-fold increase in MV in some adults during intense exercise, from six liters of air per minute at rest to 150 liters of air per minute. The increase in tidal volume is responsible for most of the dramatic increase in MV, not the increase in breathing rate.

The stimulus for increasing the MV during exercise is not well-understood. Carbon dioxide is the most well-known stimulator of the respiratory control centers of the central nervous system, but the level of carbon dioxide in the blood does not rise much during exercise, due to its rapid expiration in the lungs. The stimulus may proceed from proprioceptors of muscle activity or from an increase in blood potassium during muscular activity.

As the MV increases during exercise, the amount of blood perfused through the lungs increases proportionately. To pump the blood faster, the cardiac output (CO)—the heart rate multiplied by the stroke volume of the heart-increases during exercise. The heart rate may increase from approximately 60 beats per minute to approximately 200 beats per minute in a healthy young adult. Adult heart rates above 200 beats per minute do not increase CO further as the heart does not have time to fill properly. The stroke volume of the heart may increase from approximately 80 milliliters (mls) per beat to approximately 150 ml per beat in athletes. This allows the CO to vary from approximately 5 liters/minute at rest to approximately 30 liters per minute during intense exercise. It is difficult to appreciably increase the heart rate and stroke volume beyond the values above. If the myocardium is stretched beyond the maximum stroke volume, the heart and its pumping action get weaker, not stronger. Hence, the cardiovascular system and not the respiratory system may be the limiting factor in how intensely a patient can exercise.

The MV (which is a measure of ventilation) and the CO (which is a measure of blood perfusion) can have the same units—liters per minute. As exercise commences, the ideal 1:1 ratio between ventilation and perfusion remains linear. As exercise progresses, MV increases rapidly-both the breathing rate and the tidal volume increase together. The consumption of oxygen ($VO_2$) and the MV remain linearly related, until humans reach between 55-75% of their maximum ability to work and to consume oxygen ($VO_2$ max). Beyond this 55-75% level of $VO_2$ max—a level known as the "ventilatory breakpoint"—the MV rises exponentially. The departure of MV from a linear relationship with $VO_2$ after the breakpoint is thought to occur to increase evaporative heat loss from the lungs during intense exercise, and to increase the expiration of carbon dioxide, which lowers the concentration of H+ ions generated by increasing levels of lactic acid from the muscles. Thus, during exercise, there are many factors that could affect the relationships between heart rate, breathing rate, and tidal volume in a cardiac patient. The same is true during sleep apnea.

Sleep apnea is a serious malady, especially for those afflicted with heart failure. Symptoms of sleep apnea include not only the well-known cessation of breathing but also snoring, breath holding, rapid awakening, headaches, and more chronically, depression, irritability, fatigue, and memory loss.

Apnea is deemed to be present when dyspnea, that is, breathing difficulty, causes blood oxygenation and tissue oxygen saturation to decrease, sometimes to harmful levels. When apnea occurs, control centers in the brain react with a mild shock reaction, which can include release of norepinephrine, thereby arousing the apneic patient. Regular breathing ensues for a while with normal exchange of oxygen and accumulated carbon dioxide. Severe sleep apnea, however, may result in hundreds of episodes of oxygen desaturation during a night's sleep. Many apneics are not aware of the nightly malady, and are baffled during the daytime as they experience the long term effects of their condition. Sleep apnea can be classified as "obstructive" if the sleep apnea results from mechanical airway blockage, for example, due to partial collapse of the trachea during sleep or as "central" if the condition results from neurological dysfunction higher up in the central nervous system. "Mixed" sleep apnea includes a combination of mechanical and neurological causes. Sleep apnea can be life-threatening when it occurs in conjunction with coronary artery disease (CAD) or congestive heart failure (CHF or "heart failure"). Not only does sleep apnea place a tremendous burden on the heart and the entire cardiopulmonary system directly, but also circumvents normal sleep architecture, which affects the heart indirectly when ineffective sleep is chronic. Apneics, because of low blood oxygenation, are at an increased risk for hypertension, arrhythmias, heart attack, and stroke.

Approximately fifty percent of patients with heart failure suffer from sleep apnea, including approximately ten percent who suffer from obstructive type sleep apnea and approximately forty percent who suffer from central type sleep apnea. Sleep apnea and certain types of CHF exacerbate each other because of a negative synergy between the gas exchange problem during apnea and the oxygen distribution problem characteristic of CHF.

CHF is a condition in which a weakened heart cannot pump enough blood to body organs. Heart failure may affect either the right side, left side, or both sides of the heart. The weak pumping action causes fluid to back up into other areas of the body including the liver, gastrointestinal tract, and extremities (right-sided heart failure), or the lungs (left-sided heart failure). Heart failure patients have characteristic pulmonary edema or pitting edema of the lower legs.

For many heart patients who lack effective respiration, the above-described states of sleep apnea and physical exercise present challenges and opportunities in breathing rate regulation. Because the heart and lungs are intimately related members of the cardio-pulmonary system, a normal heart rate for a given physical state should provide a good basis for regulating a corresponding breathing rate, but more sophisticated techniques are needed to effectively link a given effective heart rate with a complementary effective breathing rate during times of stress, such as sleep apnea or exercise.

SUMMARY

Heart rate information is used at least in part to obtain respiratory parameters for respiratory pacing. In various implementations, respiratory parameters, such as a target breathing rate may be delivered by an implantable device to a patient during periods of altered respiration, such as sleep apnea or exercise. The respiratory parameters may also be obtained from a patient's physical activity level, or metabolic demands.

DETAILED DESCRIPTION

Overview

In the following discussion, exemplary devices, methods, and relationships are described for obtaining target respiratory parameters, such as breathing rate and tidal volume, from heart rate and/or other physiological attributes. The target respiratory parameters can be applied in patients suffering respiratory insufficiency. For example, patients suffering from heart failure may need assistance generating effective respiratory cycles during exercise and during episodes of sleep apnea. Deriving one or more respiratory parameters from a patient's heart rate or other information and applying the derived parameters to the patient's respiration may help the patient breathe more normally during the times of increased physical activity or during sleep apnea.

Figure 1:
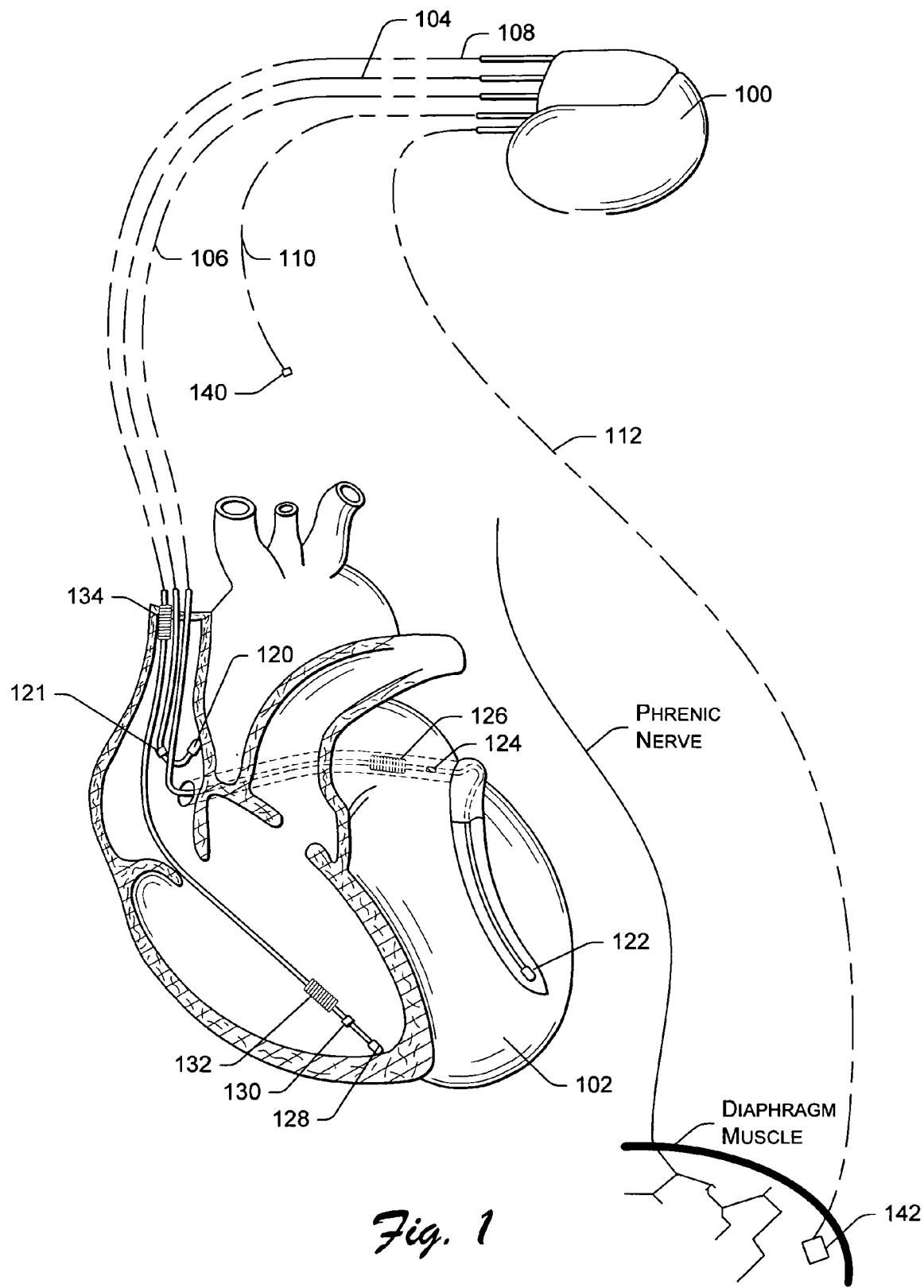
FIG. 1 is a diagrammatic illustration of an exemplary implantable cardiac device in electrical communication with a patient's heart for multi-chamber sensing and delivery of multi-chamber stimulation, as well as delivery of stimulation to control respiratory parameters.

FIG. 1 shows an exemplary device 100, which in one implementation has a sleep apnea mode and an exercise mode, that may implement the exemplary techniques and relationships described herein. When used during sleep apnea, the exemplary device 100 administers or senses a rest mode heart rate and obtains one or more target respiratory parameters, such as a target breathing rate value, based on the heart rate. If the patient's native respiration is insufficient during sleep apnea, the device applies stimulation to induce respiration in the patient based on the target respiratory parameter values, either by stimulating in order to start a respiratory cycle that the patient's own respiratory mechanism can complete, or by stimulating not only the start but the patient's entire respiratory cycle, i.e., not only the initiation of breathing, but perhaps the breathing rate, the tidal volume, and/or the entire respiratory cycle. When the exemplary techniques and relationships are used during exercise, target respiration parameters, such as a target breathing rate and/or a target tidal volume, may be obtained based on an increased exercise heart rate. If the patient's innate ventilation during exercise is insufficient, then a device, such as the exemplary device 100, applies the target breathing rate and/or tidal volume to perform respiration in the patient. Alternatively, during exercise, an exemplary device 100 may generate a target breathing rate and a target tidal volume based on projected and/or measured metabolic needs—not just on increased heart rate. Since workload and oxygen consumption are proportional to metabolic needs, a myriad of variables related to workload and oxygen consumption can be measured to generate the target exercise breathing rate and target tidal volume.

It should be noted that the respiration parameters, such as breathing rate and tidal volume, are applied to the phrenic nerve, to the diaphragm muscle, and/or to other bodily structures that can induce and/or perform respiration in the patient, for example, other respiratory control centers higher up in the central nervous system, and other structures that directly or indirectly affect respiration, such as hormonal control centers or receptors, etc. The subject matter is not limited to stimulating respiration in a patient's lungs via the phrenic nerve or the diaphragm, although these structures are readily available pathways for inducing and controlling respiration.

An environmental context in which an exemplary device 100 may be used will be described first followed by a description of exemplary components in an exemplary device 100. Then techniques and relationships for obtaining target respiration parameters, such as target breathing rates, target tidal volumes, and/or target minute ventilation values will be discussed.

Exemplary Device

An implantable device, such as exemplary device 100, is often characterized as a miniature computing device implanted into the body of a patient to monitor, regulate, and/or correct cardiac, respiratory, and other activity. Such an exemplary device 100 may include cardiac stimulation components (e.g., pacemaking and defibrillating components). The following discussion describes first an exemplary device 100 that is effective for treating cardiac conditions, such as those related to heart failure, and then a describes modes of operation in which parameters for controlling respiration may be obtained.

FIG. 1 further shows an exemplary device 100 in electrical communication with a patient's heart 102 for monitoring heart activity and/or delivering stimulation therapy, such as pacing and/or respiratory therapies. Three leads—a right atrial lead 104, a coronary sinus lead 106, and a right ventricular lead 108—interconnect the exemplary device 100 with the patient's heart 102 to support multi-chamber detection and stimulation therapy. Additional leads may be used for other electrical and chemical sensors located inside or outside the heart, such as a blood chemistry sensor lead 110 and a respiratory control lead 112.

The right atrial lead 104 supports an atrial tip electrode 120, which typically is implanted in the patient's right atrial appendage. The right atrial lead 104 also supports a right atrial ring electrode 121, which enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the exemplary device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy. In some implementations, one of the aforementioned electrodes on the coronary sinus lead 106 additionally stimulates respiration via the phrenic nerve which lies near the heart.

The right ventricular lead 108 is electrically coupled to a right ventricular tip electrode 128, a right ventricular ring electrode 130, a right ventricular (RV) coil electrode 132, and a superior vena cave (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

A blood chemistry sensor lead 110 can be positioned to allow one or more blood chemistry sensor probe(s) 140 to come in contact with arterial or venous blood. A suitable location may be in a major artery or a pulmonary vein, depending on the size and shape of the blood chemistry sensor probe(s) 140. Alternatively, the coronary sinus lead 106 could be used to couple a blood chemistry sensor probe 140 with the exemplary device 100. The type of blood chemistry sensor probe 140 and its specific location depends on the type of test being performed. One or more blood chemistry sensor probe(s) 140 may test for pH level, oxygen saturation, carbon dioxide level, etc.

In some implementations, one or more apnea detection lead(s) (not shown) may be positioned to facilitate detection and/or measurement of sleep apnea, e.g., via physiological sensors 270. Since there are many ways to measure sleep apnea, placement of lead(s) depends on sensor(s) selected. If transthoracic impedance is used to detect or measure sleep apnea, then apnea detection lead(s) may not be needed if transthoracic impedance can be measured through electrodes coupled with leads 104, 106, 108. If an apnea symptom being used as a measure of sleep apnea involves, for example, abdominal or leg movements, then an apnea symptom sensor may be a motion detector placed outside the heart.

In some implementations, one or more respiratory control lead(s) 112 may be positioned to facilitate stimulation and/or induction of respiration via a respiratory control probe 142. There are several ways to induce or otherwise control respiration and/or specific respiration parameters. Accordingly, if respiration is controlled by stimulating the diaphragm muscle, then a respiratory control probe 142 may consist of intramuscular diaphragm electrode(s) located on, in, or near the diaphragm muscle. If respiration is controlled via phrenic pacing via a patient's phrenic nerve, then a respiratory control probe 142 may be placed somewhere along a patient's phrenic innervation. Alternatively, since the route of the phrenic nerve is near the heart, in some implementations respiratory control may be achieved, as mentioned above, via an electrode attached to a coronary sinus lead 106 without need for a dedicated respiratory control lead 112 and a dedicated respiratory control probe 142.

Figure 2:
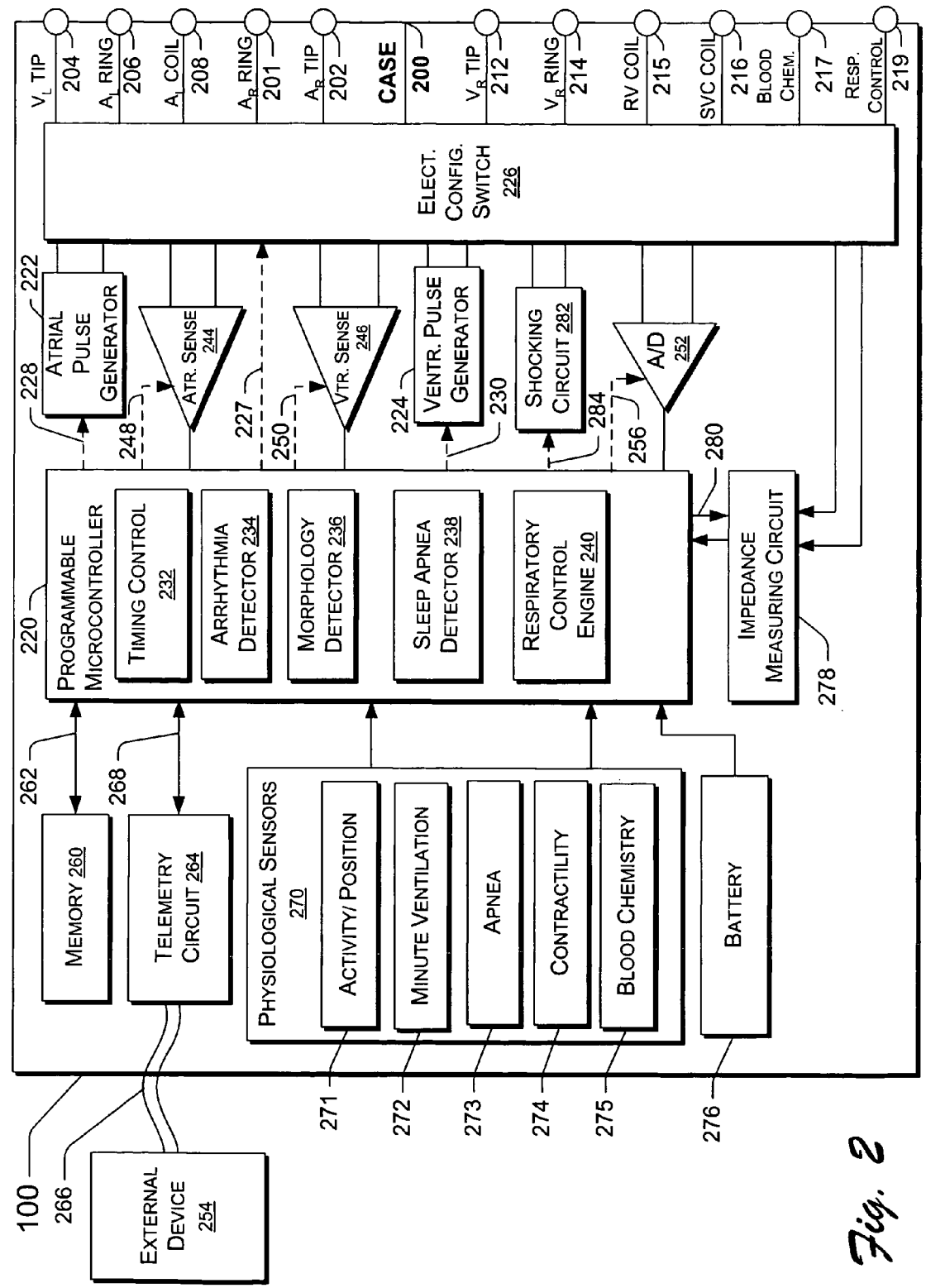
FIG. 2 is a functional block diagram of the exemplary device of FIG. 1.

FIG. 2 shows an exemplary block diagram depicting various components of the exemplary device 100. The components are housed in a case 200, which is often referred to as the "can", "housing", "encasing", or "case electrode", and may be programmably selected to act as the return electrode for unipolar operational modes. The case 200 may further be used as a return electrode alone or in combination with one or more of the coil electrodes 126, 132 and 134 for stimulating purposes. The case 200 further includes a connector (not shown) having a plurality of terminals 201, 202, 204, 206, 208, 212, 214, 215, 216, 217, and 219 shown schematically with the names of the electrodes to which they are connected shown next to the terminals, including:

a right atrial ring terminal ($A_R$ RING) 201 for atrial ring electrode 121;

a right atrial tip terminal ($A_R$ TIP) 202 for atrial tip electrode 120;

a left ventricular tip terminal ($V_L$ TIP) 204 for left ventricular tip electrode 122;

a left atrial ring terminal ($A_L$ RING) 206 for left atrial ring electrode 124;

a left atrial shocking terminal ($A_L$ COIL) 208 for left atrial coil electrode 126;

a right ventricular tip terminal ($V_R$ TIP) 212 for right ventricular tip electrode 128;

a right ventricular ring terminal ($V_R$ RING) 214 for right ventricular ring electrode 130;

a right ventricular shocking terminal (RV COIL) 215 for RV coil electrode 132;

an SVC shocking terminal (SVC COIL) 216 for SVC coil electrode 134;

a blood chemistry terminal 217 for blood chemistry sensor probe(s) 140; and a respiratory control terminal 219 for respiratory control probe(s) 142.

An exemplary device 100 may include a programmable microcontroller 220 that controls various operations of the implantable cardiac device, including cardiac, respiratory, and metabolic monitoring and cardiac and respiratory stimulation therapy. Microcontroller 220 includes a microprocessor (or equivalent control circuitry), RAM and/or ROM memory, logic and timing circuitry, state machine circuitry, and I/O circuitry.

An exemplary device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The electrode configuration switch 226 may include multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 220 is also equipped with an arrhythmia detector 234, a morphology detector 236, a sleep apnea detector 238, and a respiratory control engine 240. The sleep apnea detector 238 is configured to diagnose current episodes of sleep apnea and, in some implementations, even anticipation of or the initial onset of an episode of sleep apnea.

There are multiple ways of sensing sleep apnea and multiple techniques for ascertaining a metric known as "apnea burden." For example, apnea burden can be time spent in apnea per hour. An exemplary sleep apnea detector 238 can use measurements of one or more symptoms suggestive of apnea to measure apnea burden. For instance, the detector might detect changes in respiration, heart rate, thoracic impedance, physical activity (abdominal movement, leg jerking), blood chemistry, and/or minute ventilation as being suggestive of sleep apnea. Frequent arousals from sleep are also indicative of sleep apnea and can be measured by an accelerometer, e.g., an activity/position sensor 271. In another approach, the sleep apnea detector 238 detects coinciding changes of two or more parameters that indicate onset of sleep apnea and are viable for apnea burden measurements. For instance, a sleep apnea detector 238 may anticipate an upcoming sleep apnea episode if the patient, while resting, experiences a decrease in minute ventilation and a concurrent drop in heart rate. In another approach, the sleep apnea detector 238 uses pattern analysis to anticipate sleep apnea. In this case, the sleep apnea detector 238 compares current physiological parameters with patterns of the same parameters captured during previous sleep apnea episodes to determine whether the current parameters suggest onset of sleep apnea.

If transthoracic impedance measurements are used to diagnose sleep apnea or measure apnea burden, an exemplary sleep apnea detector 238 may employ data from an impedance measuring circuit 278, and/or a minute ventilation detector 272, to track breathing rate and/or tidal volume. If a change in blood chemistry is being used to diagnose sleep apnea or measure apnea burden, an exemplary sleep apnea detector 238 may use in vivo measurements from a blood chemistry sensor probe 140 to detect an episode of sleep apnea and/or measure apnea burden. There are many chemical components of a patient's blood that change concentration, level, or saturation when the patient lapses into sleep apnea, such as oxygen, carbon dioxide, hydrogen ion, hydroxide ion, bicarbonate ion, etc. Each of these can be measured (e.g., pH, pOH, $pCO_2$, $O_2$ saturation, etc.) and compared to known thresholds or patient baseline values to diagnose the presence and/or duration of a sleep apnea episode. Once a particular chemical species is adopted to diagnose sleep apnea, a suitable blood chemistry sensor probe 140 for that chemical species may be selected to measure a concentration of the chemical species.

Alternatively, an exemplary sleep apnea detector 238 may avail of cardiac contractility information from a contractility sensor 274 in addition to or instead of other apnea symptoms, e.g., as a surrogate for apnea burden. Cardiac contractility changes during episodic sleep apnea. Frequent changes in contractility are an indicator of apnea burden and an elevation in contractility often occurs late in an apnea cycle. Contractility and other surrogates of apnea burden can be measured using intracardiac impedance measurements (see U.S. Pat. No. 5,800,467 to Park and Bornzin), by an intracardiac accelerometer, or by an accelerometer in the pacemaker case 200 that measures the impulse associated with the first heart sound. Conventionally, contractility may also be measured by using an implantable pressure transducer that measures the maximum change in pressure as a function of time (dP/dt) in the right or left ventricle.

The respiratory control engine 240 includes logic, tables, algorithms, etc., to perform exemplary methods and derive target respiratory parameters from exemplary relationships. Such exemplary methods, techniques, and relationships are illustrated in FIGS. 3-17 and described in accompanying text.

The components 232, 234, 236, 238, and 240 may be implemented in hardware as part of the microcontroller 220, or as software/firmware instructions programmed into the device and executed on the microcontroller 220 during certain modes of operation. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power, precision amplifiers with programmable gain and/or automatic gain control, bandpass filtering, and a threshold detection circuit to selectively sense the cardiac signal of interest. The automatic gain control enables the exemplary device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 220 over signal lines 248 and 250 for purposes of controlling the gain and/or threshold of polarization charge removal circuitry (not shown) and the timing of any blocking circuitry (not shown) coupled to the inputs of the sensing circuits 244, 246.

Cardiac signals are supplied to an analog-to-digital (A/D) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

The microcontroller 220 is further coupled to a memory 260 by a suitable data/address bus 262. The programmable operating parameters used by the microcontroller 220 are stored in memory 260 and used to customize the operation of the exemplary device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of an exemplary device 100 may be non-invasively programmed into the memory 260 through a telemetry circuit 264 in telemetric communication via communication link 266 with the external device 254, such as a programmer, local transceiver, or a diagnostic system analyzer. The microcontroller 220 activates the telemetry circuit 264 with a control signal 268. The telemetry circuit 264 allows intracardiac electrograms and status information relating to the operation of the exemplary device 100 (as contained in the microcontroller 220 or memory 260) to be sent to the external device 254 through an established communication link 266.

The exemplary device 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators 222 and 224 generate stimulation pulses. While shown as being included within the exemplary device 100, the physiologic sensor(s) 270 may also be external to the exemplary device 100, yet still be implanted within or carried by the patient.

Illustrated physiological sensors 270 include an activity/position sensor 271 (e.g., 3D accelerometer, movement sensor, etc.) to detect changes in the patient's position, and a minute ventilation (MV) sensor 272 to sense breathing. Minute ventilation is the total volume of air that moves in and out of a patient's lungs in a minute. The MV sensor 272 may use transthoracic impedance, which is a measure of impedance across the chest cavity, to sense air movement. Lungs filled with air have higher impedance than empty lungs. Thus, upon inhalation, impedance increases and upon exhalation, impedance decreases.

Other illustrated physiological sensors 270 include apnea sensors 273, contractility sensor(s) 274, and blood chemistry sensors 275. Still other physiologic sensors and sensing circuits can also be included.

Signals generated by the physiological sensors 270 are passed to the microcontroller 220, for example, for analysis by the sleep apnea detector 238 and/or the respiratory control engine 240. Such signals can be used to determine whether the patient is at rest or exercising, whether the patient is experiencing an episode of sleep apnea, and whether to invoke any responsive therapy prescribed by the respiratory control engine 240.

The implantable cardiac device 100 additionally includes a battery 276 that provides operating power to the components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected. As one example, the exemplary device 100 employs lithium/silver vanadium oxide batteries.

The exemplary device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The exemplary device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 278 is coupled to the switch 226 so that any desired electrode may be used.

The exemplary device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 joules), moderate (e.g., 0.5-10 joules), or high energy (e.g., 11 to 40 joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the case 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of, e.g., 5-40 joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

An exemplary device 100 can be programmed to treat both heart failure and respiratory deficiency. To treat heart failure, the device typically delivers pacing pulses of a voltage level via a lead, such as the coronary sinus lead 106, in the left-sided veins.

More generally, the exemplary device 100 can be programmed to stimulate different sets of cardiac muscles and/or respiratory muscles (i.e., the diaphragm) through a lead/electrode system. The exemplary device 100 can be programmed to vary the output voltage of various pulses to effectively stimulate different muscles of the heart and the diaphragm, even though the lead and electrode placement may or may not change.

Methods and Relationships for Obtaining a Respiratory Parameter

Figure 3:
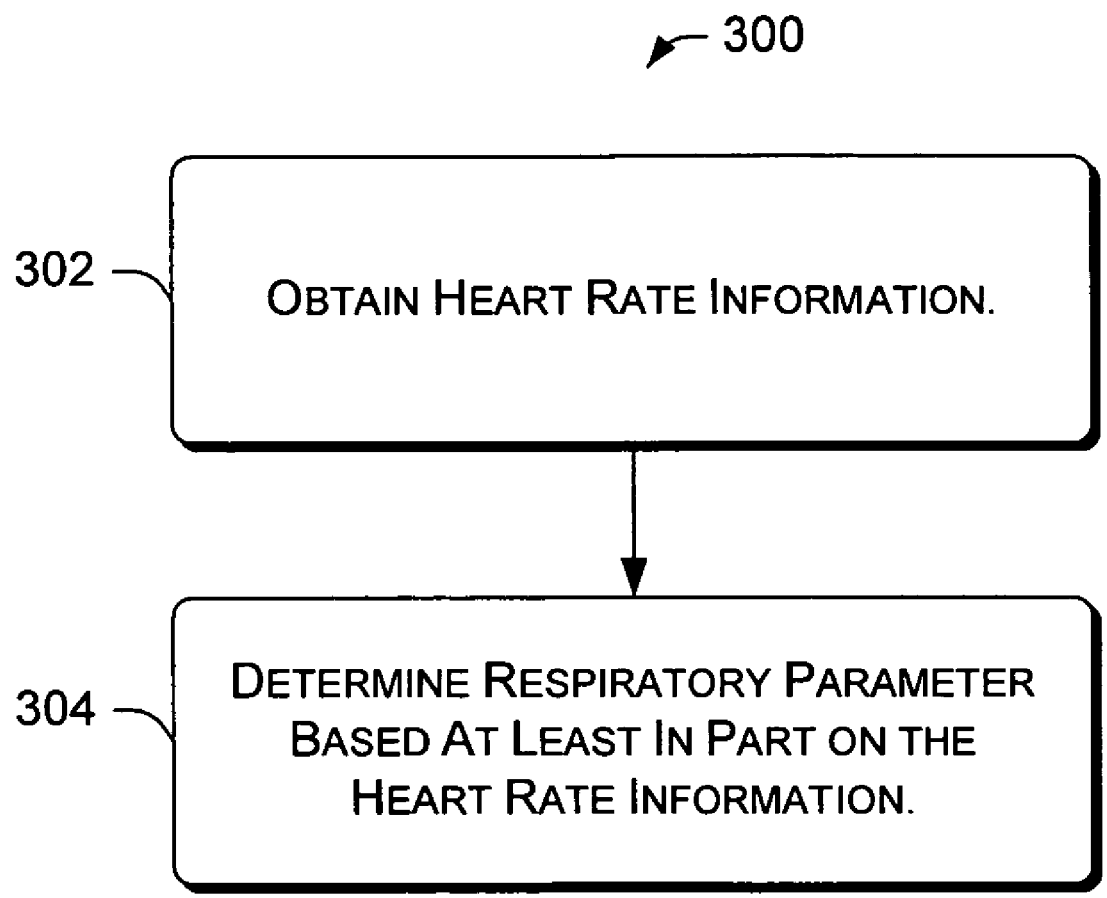
FIG. 3 is a flow diagram of an exemplary method for determining a breathing rate parameter at least in part from heart rate information.

FIG. 3 shows an exemplary method 300 for determining a target respiratory parameter, for example a patient's breathing rate. According to this exemplary method 300, an implantable device, such as the exemplary device 100, is programmed to apply cardiac pacing pulses to treat a heart condition and to generate a target respiratory parameter if the patient's respiration is insufficient, e.g., during episodes of sleep apnea or during exercise.

In the flow diagram, the operations are summarized in individual blocks. The operations may be performed in hardware and/or as machine-readable instructions (software or firmware) that can be executed by a device, such as an exemplary device 100 that includes a microcontroller 220.

At block 302, heart rate information is obtained for the patient, upon which a breathing rate or other respiratory parameter will be based. The heart rate information may include pacing rate information selected by a device, such as an exemplary device 100, for instance, a base pacing rate selected for patient rest or a therapeutic pacing rate to treat or prevent an episode of sleep apnea. That is, pacing devices can apply a different baseline cardiac pacing rate during sleep, and yet again another different pacing rate in an attempt to treat or prevent episodes of sleep apnea. An exemplary device 100 selecting the patient's pacing rate instead of sensing a native heart rate, may base the selection of the pacing rate, and thus the derived breathing parameter, at least in part on other criteria, e.g., input from the physiological sensors 270.

The heart rate information, as mentioned, can also be obtained by sensing the patient's native heart rate. In one implementation, if the patient has a stable sinus rhythm the exemplary device 100 takes a rolling average of the heart rate over approximately six to approximately twelve beats. Multiple beats are averaged because the instantaneous heart rate varies considerably from beat to beat, and if used to calculate a breathing rate or other respiratory parameter, would produce wide swings. At the other extreme, if a larger number of heart beats is used to obtain an average heart rate, a device practicing an exemplary method 300 would be too slow to respond to changes in heart rate. Therefore, in one implementation, an average heart rate calculated over 6-12 beats gives a stable and representative heart rate value without undue delay. The rolling or moving average sensed heart rate may be referred to as just the "heart rate."

At block 304, a respiratory parameter is determined, at least in part, from the heart rate information. The subject matter contemplates multiple techniques for obtaining a respiratory parameter (such as a target breathing rate), from the heart rate information, as will be discussed below. An obtained target breathing rate, for example, can then be applied during an episode of sleep apnea to treat the episode or during exercise to provide respiratory activity that complements the level of cardiac activity. Since an exemplary device 100 may already be pacing a patient's heart, a suitable respiratory parameter, such as a target breathing rate, can be applied by the same exemplary device 100.

Figure 4:
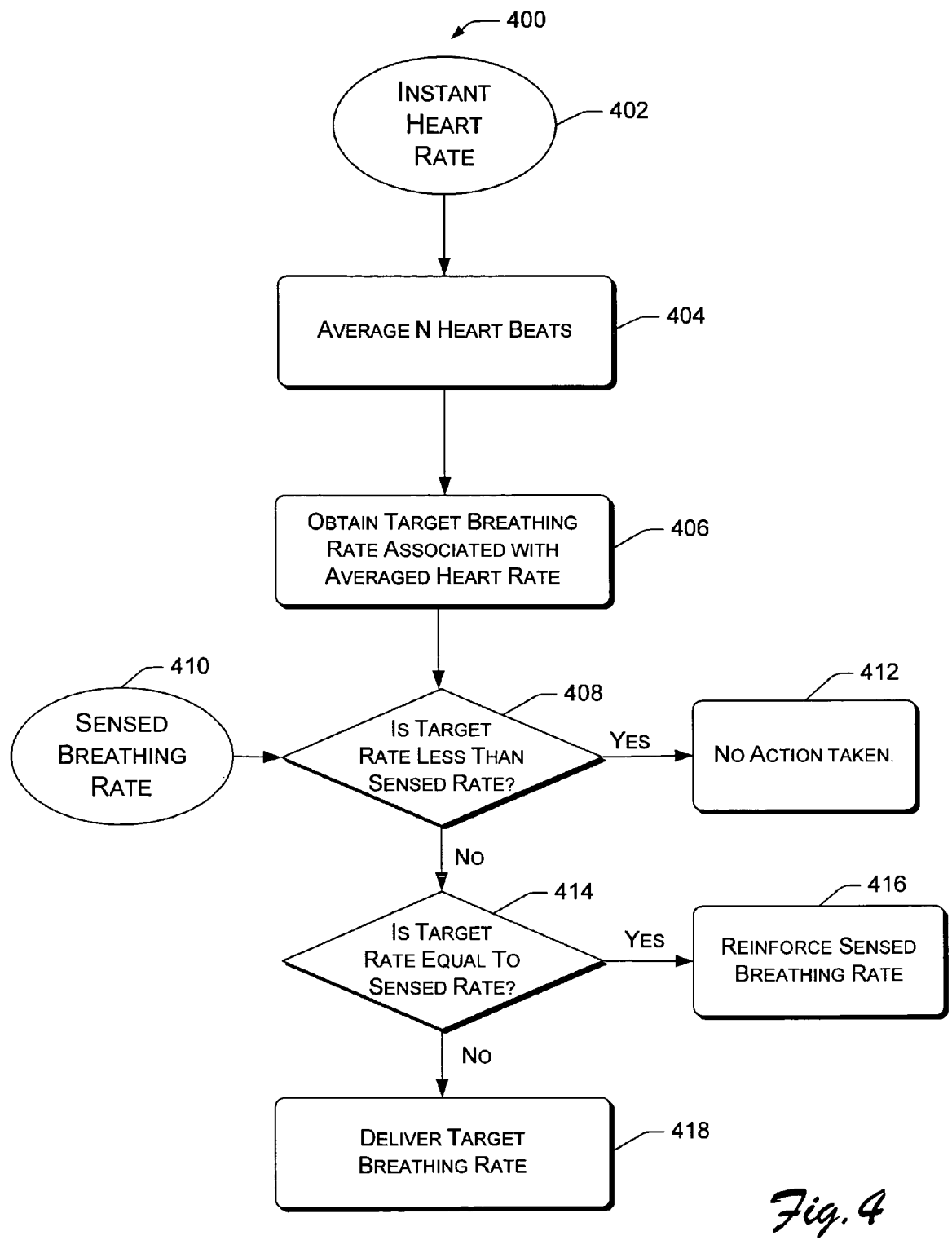
FIG. 4 is a flow diagram of an exemplary method for implementing a respiratory parameter derived from heart rate information.

FIG. 4 shows an exemplary method 400 for delivering a target respiratory parameter, in this case, a target breathing rate to complement the patient's heart rate. According to this exemplary method 400, an implantable device, such as the exemplary device 100, is programmed to apply cardiac pacing and to obtain and deliver respiratory stimulation that uses a target respiration parameter if the patient's respiration is insufficient.

In the flow diagram, the operations are summarized in individual blocks. The operations may be performed in hardware and/or as machine-readable instructions (software or firmware) that can be executed by a device, such as an exemplary device 100 that includes a microcontroller 220.

At block 404, an instant heart rate 402 of the patient, either the native heart rate or a paced heart rate, is averaged over N beats, for example, over approximately six beats or pulses.

At block 406, a target respiratory parameter, such as a target breathing rate, associated with the averaged heart rate, is obtained. In the case of a target breathing rate, an exemplary device 100 or a module in a device, such as the exemplary respiratory control engine 240, can use software and/or hardware to employ an algorithm, method, relationship, and/or transfer (translation) table, etc., as described below with regard to FIGS. 5-7 to obtain the target breathing rate from the heart rate information. A device or module, such as the exemplary respiratory control engine 240, can optionally add input from other sources, such as physiological sensors 270 into an algorithm or transfer table scheme embodying a relationship to obtain a target breathing rate.

At a decision block 408, the target respiratory parameter, such as breathing rate, obtained in block 406 is compared with a corresponding sensed respiratory parameter, such as sensed breathing rate 410. If a target breathing rate, for example, is less than a sensed breathing rate 410, then in one implementation the exemplary device 100 does nothing, at block 412. The patient is already breathing using a satisfactory respiration parameter, such as a breathing rate that surpasses the target breathing rate, so no application of the target respiratory parameter (e.g., breathing rate) is needed.

Using breathing rate as an example respiratory parameter, if the target breathing rate is not less than the sensed breathing rate, then in some implementations the target breathing rate may be used to stimulate the patient's phrenic nerve or diaphragm, or, as illustrated in FIG. 4, a second comparison may be used to further distinguish whether the difference between the target breathing rate and the sensed breathing rate 410 is great enough to warrant applying the target breathing rate.

At block 414, if the target breathing rate and the sensed breathing rate 410 are substantially equal, then at block 416 stimulation may be applied to reinforce the patient's native breathing rate. Alternatively, no action may be taken at block 416 if the patient does not need the native breathing rate to be reinforced.

If the target breathing rate and the sensed breathing rate 410 are not substantially equal, e.g., within a predetermined margin of variance, then at block 418 the target breathing rate is delivered.

When delivering a target breathing rate, a conversion factor of sixty seconds per minute may be divided by the target breathing rate to obtain a breath interval for delivering respiratory pulses to induce respiration in the patient, e.g., via the phrenic nerve or diaphragm.

Figure 5:
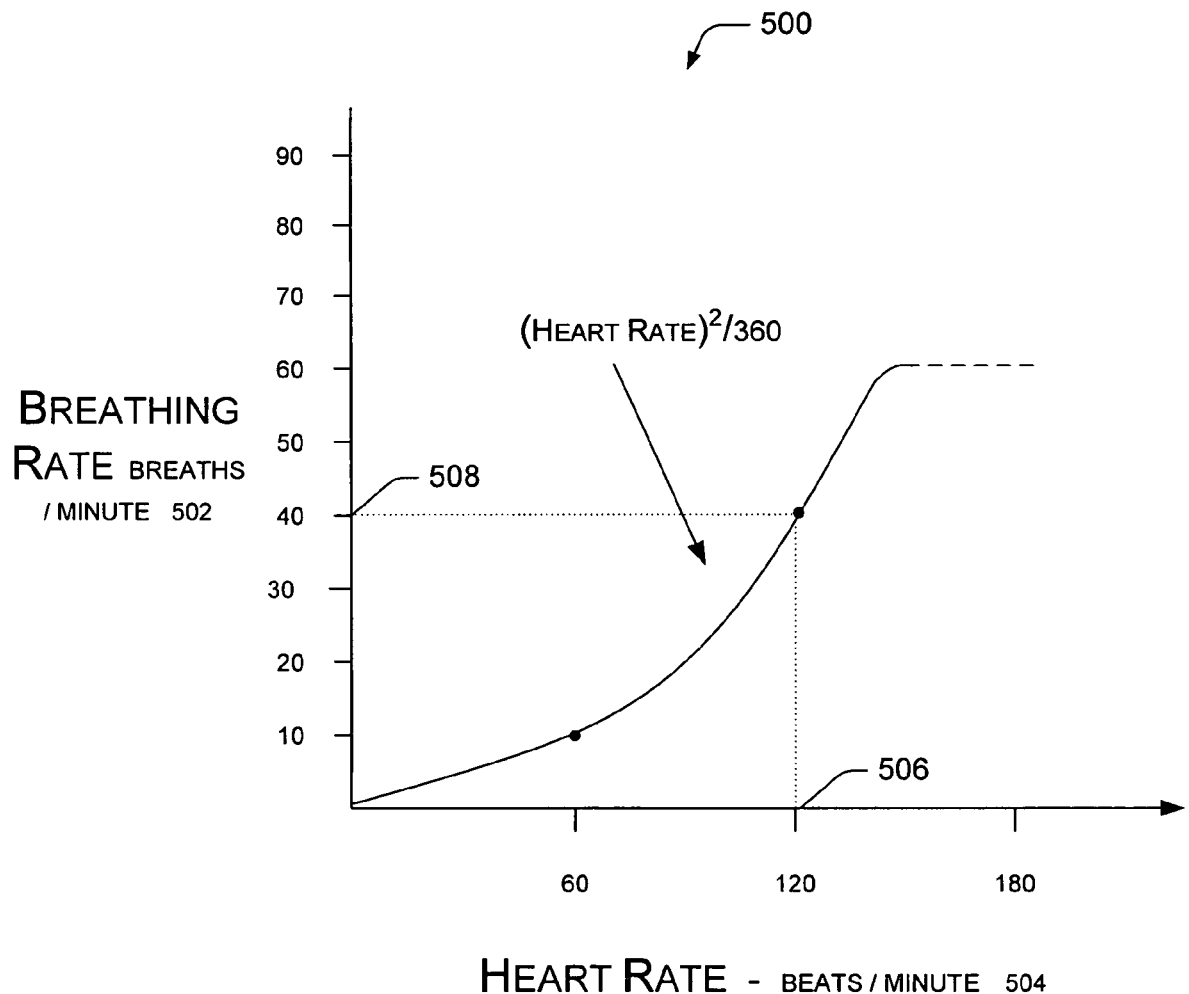
FIG. 5 is a graphical representation of a first exemplary relationship for associating breathing rate with heart rate.

FIG. 5 shows an exemplary relationship 500 for associating breathing rate 502 to heart rate 504 for use in selecting a target breathing rate. In this exemplary relationship 500, heart rate 504 is related to breathing rate 502 by equation (1):

$$\text{Breathing rate} = (\text{Heart Rate})^2/360 \qquad \text{Equation (1)}$$

Equation (1) is one approximation of how a natural breathing rate might vary as heart rate increases. In an example solution of equation (1), a heart rate value of 120 beats per minute (506) yields an associated target breathing rate of 40 breaths per minute (508). The exemplary relationship 500 uses a sixty breath per minute ceiling on the breathing rate 502 despite further increases in the heart rate 504 as this breathing rate is rarely exceeded, even in athletes.

Figure 6:
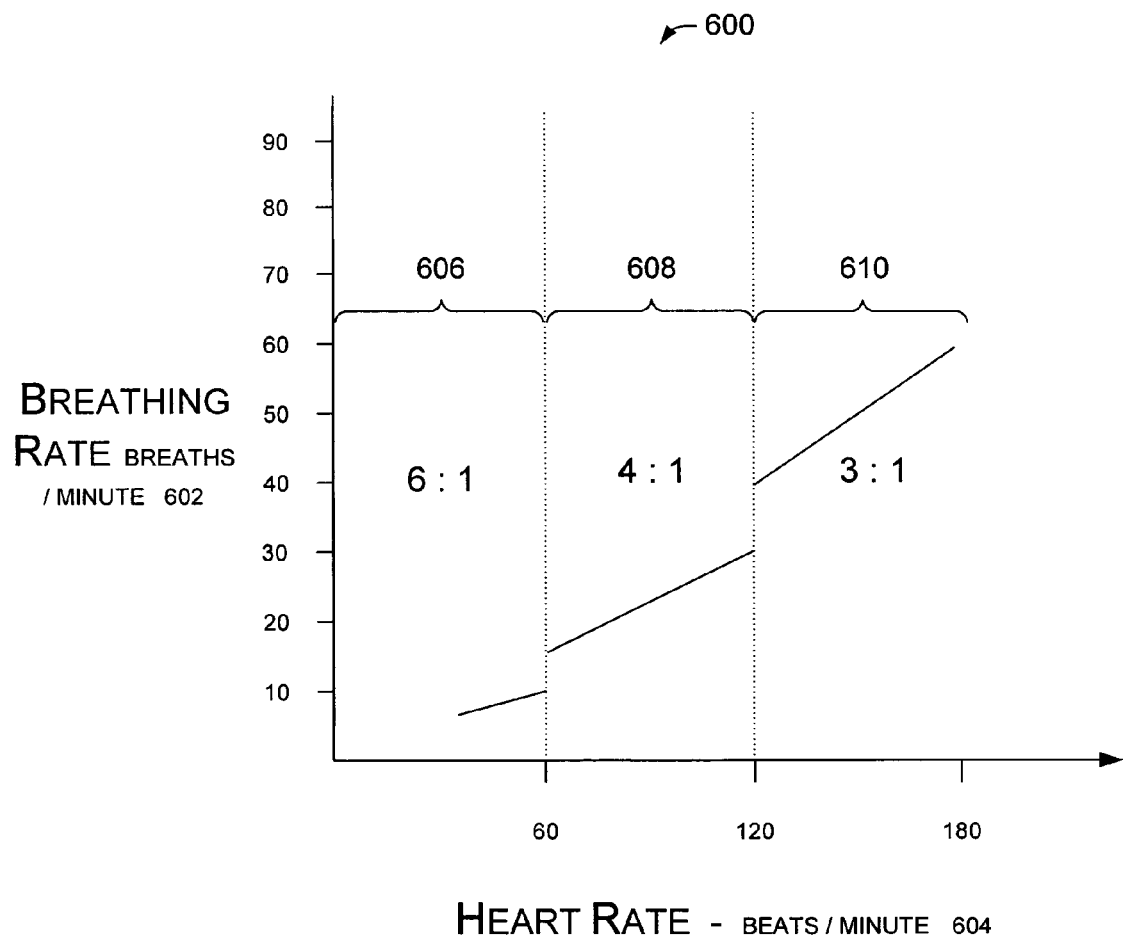
FIG. 6 is a graphical representation of a second exemplary relationship for associating breathing rate with heart rate.

FIG. 6 shows another exemplary relationship 600 for associating breathing rate 602 to heart rate 604 for use in selecting a target breathing rate. In this exemplary relationship 600, integral ratios of "heart beats per breath" are assigned to incremental ranges of heart rates to approximate how natural breathing rate might vary as heart rate increases. For example, exemplary heart rate ranges of "40-60 beats per minute" 606, "61-119 beats per minute" 608, and "120 or more beats per minute" 610 have exemplary "heart beats per breath" ratios of 6:1, 4:1, and 3:1, respectively. Each individual heart rate within one of the ranges can be associated with a target breathing rate using the range's assigned ratio. For example, if the heart rate is 60 beats per minute a 6:1 heart beats per breath ratio is applied and the target breathing rate is 10 breaths per minute; if the heart rate is 120 beats per minute a 4:1 ratio is applied and the target breathing rate is 30 breaths per minute; and if the heart rate is 180 beats per minute a 3:1 ratio is applied and the target breathing rate is 60 breaths per minute. Of course, a different number of ranges could be used and each range could encompass different heart rates than the illustrated exemplary heart rate ranges 606, 608, 610.

Figure 7:
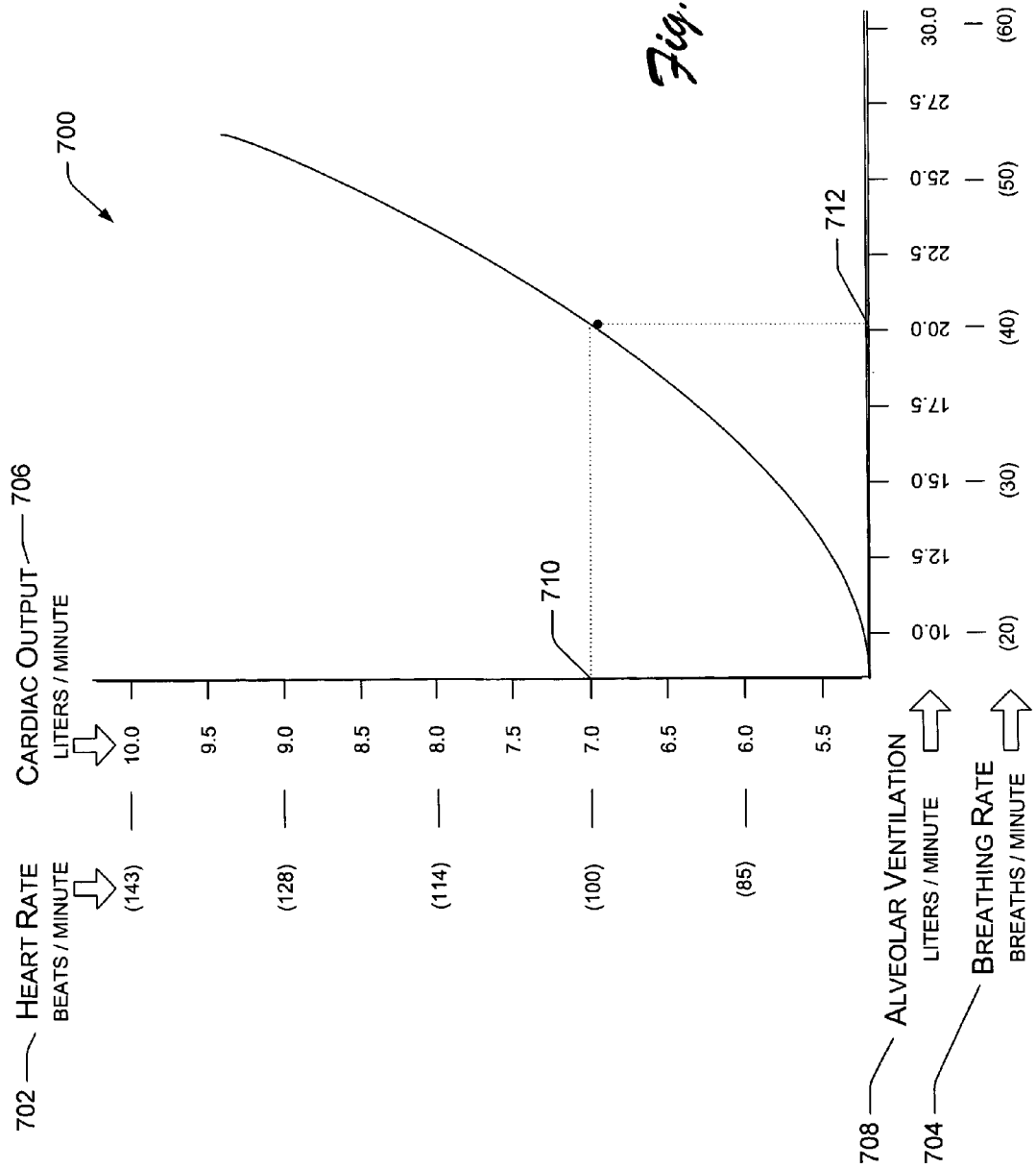
FIG. 7 is a graphical representation of an exemplary relationship for associating cardiac output and heart rate to alveolar ventilation and breathing rate.

FIG. 7 shows another exemplary relationship 700 for associating heart rate 702 to breathing rate 704 for use in selecting a target breathing rate. This exemplary relationship 700 also approximates the manner in which natural breathing rate might vary as heart rate increases, however, the approximation is based on certain physiological measures of metabolic demand.

Heart rate has a linear relationship to cardiac output (CO) 706 at constant cardiac stoke volume, since CO 706 is defined as the product of the heart rate times the stroke volume. The stroke volume of each ventricle is approximately 70 milliliters on average, and although the stroke volume can change somewhat during exercise, this method assumes the stroke volume remains approximately constant. This assumption can be satisfactory and moreover fairly accurate in some heart failure patients.

The CO 706, in turn, is approximately linearly related to alveolar ventilation (VA) 708, that is, pulmonary gas exchange between the blood and the atmosphere proceeds by exposing a given volume of blood to a given amount of air per unit time. The linearity of this relationship holds until the ventilatory breakpoint, which occurs somewhere between 55-75% of the patient's $VO_2$ max. Since VA 708 equals the tidal volume (minus a dead space) times the breathing rate, this exemplary relationship 700 assumes that the tidal volume, like the cardiac stroke volume, remains constant at various breathing rates. This assumption of constant tidal volume may be accurate for some patients, especially during sleep. Alternatively, a constant tidal volume can be implemented by controlling the patient's depth of inspiration through electrical stimulation, as will be discussed below.

If an approximation is made for the sake of a particular implementation of the subject matter that both the stroke volume and the tidal volume remain constant over various ranges of heart rates and breathing rates, then the approximately linear relationship between CO 706 and VA 708 allows a target breathing rate 704 to be obtained for each heart rate 702. This exemplary relationship 700 may have the advantage of more realistically approximating the response of breathing rate to metabolic demand as represented by CO 706 and VA 708.

The set of values for CO 706 can be converted to a set of values for heart rate 702 by dividing each CO value by the constant (e.g., 70 ml) stroke volume. Likewise, if an average adult tidal volume value is held approximately constant (e.g., 500 ml), then subtracting approximately 150 ml for the dead space, a set of values for VA 708 can be converted to a set of breathing rate values by dividing each VA value by a derived constant 350 ml lung space. For example, a heart rate of 100 beats per minute 710 would have an associated VA 708 of just over 20 liters per minute corresponding to a target breathing rate 704 of just over 40 breaths per minute (712). Of course, this exemplary relationship 700 holds tidal volume constant. Since compared with changes in breathing rate 704 changes in tidal volume are much more responsible for VA 708, other exemplary relationships below include tidal volume. However, the exemplary relationship 700 described above has applicability in circumstances where a patient's tidal volume is fairly constant.

Methods for Obtaining a Target Tidal Volume

Generating a target breathing rate may not be enough for some patients suffering from dyspnea, hypopnea, apnea etc. during sleep or exercise. For example, an exercising patient with a temporarily high metabolic demand may need to have depth of inspiration controlled using a target tidal volume. A target minute ventilation (MV), therefore, can be achieved if both a target breathing rate and a target tidal volume are applied.

As mentioned above, although an average VA corresponding to a MV is approximately 5-6 liters per minute for a resting patient, an adult may increase the MV twenty-five fold—for example, up to 150 liters per minute—by increasing the breathing rate and especially by increasing the tidal volume. Changes in the tidal volume of each breath create the dramatic difference in the MV, more so than changes in the breathing rate. A shallow breath may have a tidal volume of 150 ml; a normal quiet breath may have a tidal volume of 500 ml; but a deep slow breath may have a tidal volume of 1200 ml. To illustrate how tidal volume influences MV more than breathing rate, shallow breaths taken at a relatively high breathing rate of 40 breaths per minute yield a near zero VA due to the dead space, breaths of average volume taken at a lower breathing rate of 12 breaths per minute actually yield a higher MV of, say, approximately 4200 liters/minute, and deep slow breaths taken at am even lower breathing rate of 5 breaths per minute yield a far higher MV of 5250 liters per minute. Hence, tidal volume is the most important factor between the two in achieving a target MV.

Because of the importance of tidal volume to MV, especially during critical times like exercise or sleep apnea, subject matter for achieving a target tidal volume and/or a target MV will now be described.

Figure 8:
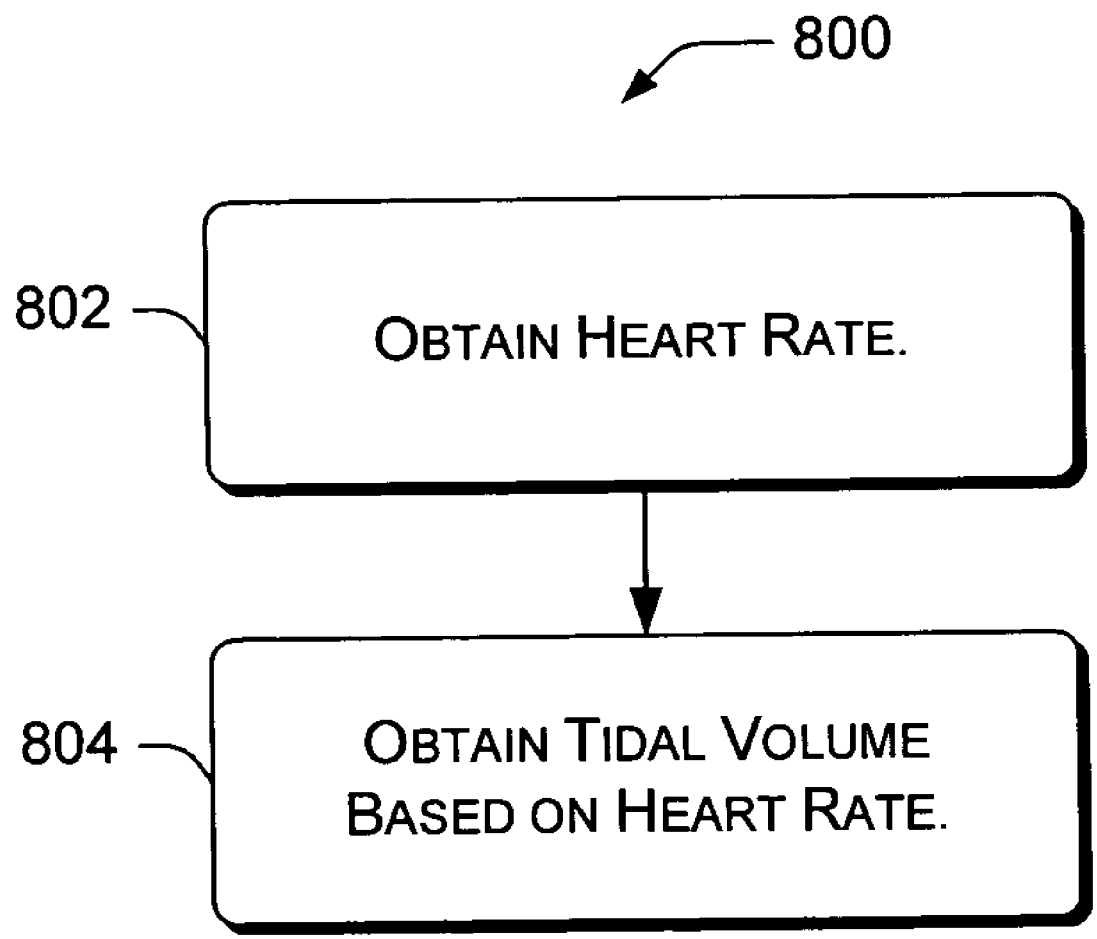
FIG. 8 is a flowchart of an exemplary method for obtaining a tidal volume parameter from heart rate information.

FIG. 8 shows an exemplary method 800 of obtaining a target tidal volume parameter for respiratory stimulation. According to this exemplary method 800, an implantable cardiac device, such as exemplary device 100, may be programmed to apply cardiac pacing pulses to treat a patient needing cardiac pacing therapy and to obtain and apply target tidal volume parameters based on the heart rate if the patient's tidal volume is insufficient during episodes of sleep apnea or during exercise.

In the flow diagram, the operations are summarized in individual blocks. The operations may be performed in hardware and/or as machine-readable instructions (software or firmware) that can be executed by a device, such as an exemplary device 100 that includes a microcontroller 220.

At block 802, a heart rate is obtained for the patient. The heart rate may be selected by an implantable device, such as exemplary device 100. The heart rate can also be obtained by sensing the patient's native heart rate, as discussed above in relation to FIG. 3.

At block 804, a target tidal volume for the patient is obtained based on the obtained heart rate. There are many ways to obtain a target tidal volume from the heart rate, for example via a table of experimental values relating tidal volume to heart rate, by assuming parallel linear increases between tidal volume and heart rate, or by relating tidal volume and heart rate to a common parametric, such as target breathing rate, metabolic demand, blood oxygen saturation, etc.

Figure 9:
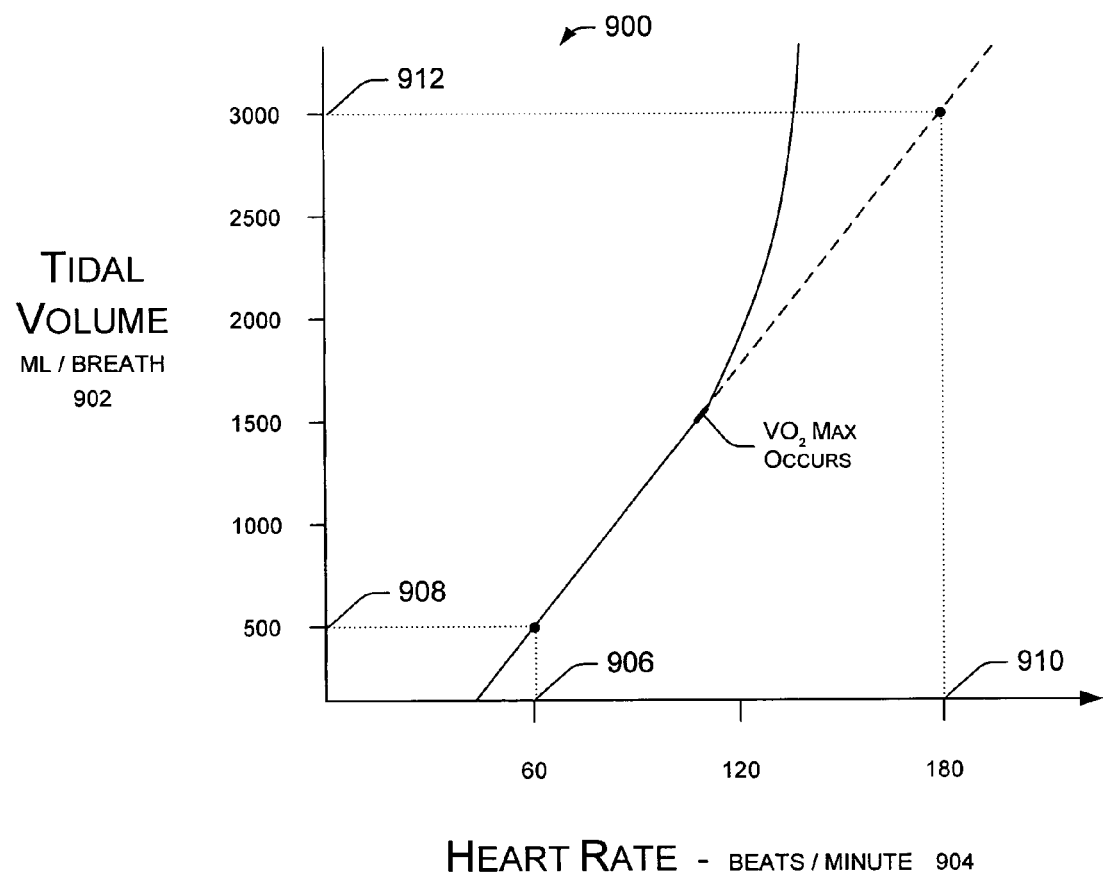
FIG. 9 is a graphical representation of an exemplary relationship for associating tidal volume with heart rate.

FIG. 9 shows an exemplary relationship 900 for associating tidal volume 902 to heart rate 904 for use in selecting a target tidal volume for respiratory stimulation based on heart rate. The exemplary relationship 900 adopts a nearly linear relationship between changes in tidal volume 902 with respect to changes in heart rate 904. In the illustrated exemplary relationship 900, the association is set up by selecting two or more known heart rates, for example heart rates that are assumed to be maximum and minimum heart rates, at which corresponding tidal volumes are either known or can be measured. For example, at a heart rate of 60 beats per minute 906 the tidal volume is set at 500 ml per breath 908, which is an average tidal volume for an adult at rest. At a heart rate of 180 beats per minute 910, which in this case is assumed to be a maximum heart rate for the patient, the tidal volume is set at a projected maximum of 3000 ml per breath 912. This selection of a tidal volume for each of two heart rates is used to establish a linear relationship from which other target tidal volumes can be obtained, given a heart rate. Although the linearity of this exemplary relationship 900 may break down above $VO_2$ max, still the exemplary relationship 900 can be useful for deriving tidal volumes for various ranges of heart rates below $VO_2$ max.

In some implementations, the exemplary relationship 900 may be cross-checked against some other physiological variable indicative of current metabolic demand, such as oxygen percentage saturation, blood pH, motion detection indicative of physical activity, cardiac contractility, etc. Monitoring other physiological variable(s) provides a cross-check in case the exemplary relationship 900 breaks down above $VO_2$ max or a fast heart rate is caused by factors other than a current high metabolic demand. For example, a high heart rate may ensue from shock, or as a side effect of taking some types of medications. To proportionately increase tidal volume in these circumstances could cause hyperventilation, respiratory alkalosis, and other undesirable side effects.

Figure 10:
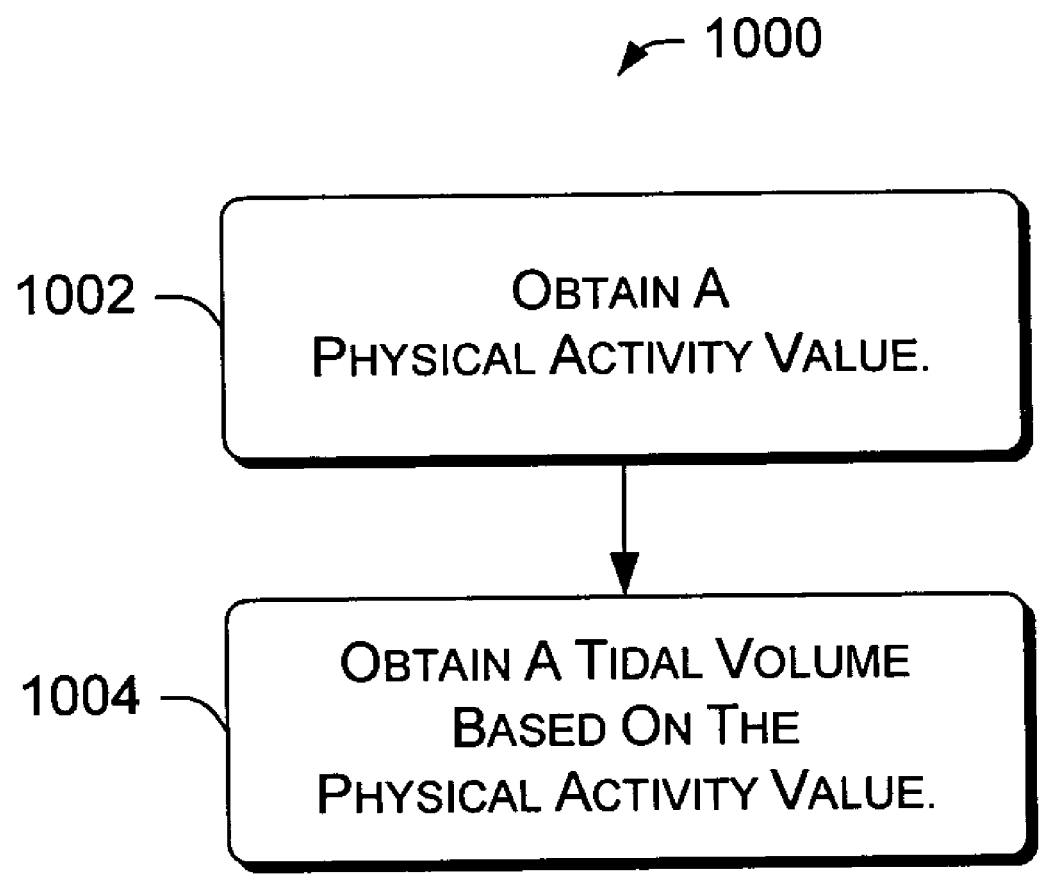
FIG. 10 is a flowchart of an exemplary method for obtaining a tidal volume parameter from physical activity level information.

FIG. 10 shows an exemplary method 1000 for obtaining a target respiration parameter, such as a target tidal volume. According to this exemplary method 1000, an implantable cardiac device, such as exemplary device 100, may be programmed to apply cardiac pacing pulses and to obtain the target tidal volume parameter if the patient's tidal volume is insufficient, e.g., during episodes of sleep apnea or during exercise.

In the flow diagram, the operations are summarized in individual blocks. The operations may be performed in hardware and/or as machine-readable instructions (software or firmware) that can be executed by a device, such as an exemplary device 100 that includes a microcontroller 220.

At block 1002, a physical activity level is obtained for a patient. If the physical activity level is determined from the patient's breathing, the breathing rate may need to be determined and may be selected, calculated, and or sensed by an implantable device, such as exemplary device 100, for example by using one of the methods described in relation to FIGS. 3-7. There are many other ways to measure and/or approximate a patient's physical activity level besides using a breathing rate and/or heart rate. For example, blood oxygen percentage saturation, blood carbon dioxide level, blood pH, heart contractility, bodily movement, etc., can be used as measures of a patient's physical activity level.

At block 1004, a target tidal volume for the patient is obtained based on a physical activity level. Obtaining the target tidal volume based on an indication of the physical activity level is reasonable because deep breathing usually accompanies increased $VO_2$, when the body requires more oxygen due to an increased metabolic demand. During exercise, increasing the tidal volume is the most efficient means of elevating MV. When tidal volume is increased, the entire increase goes toward elevating the MV, whereas an increase in the breathing rate does not go entirely to alvealor ventilation due to the dead space. Thus, as energy needs vary, both the breathing rate and tidal volume can be adjusted by the subject matter.

Figure 11:
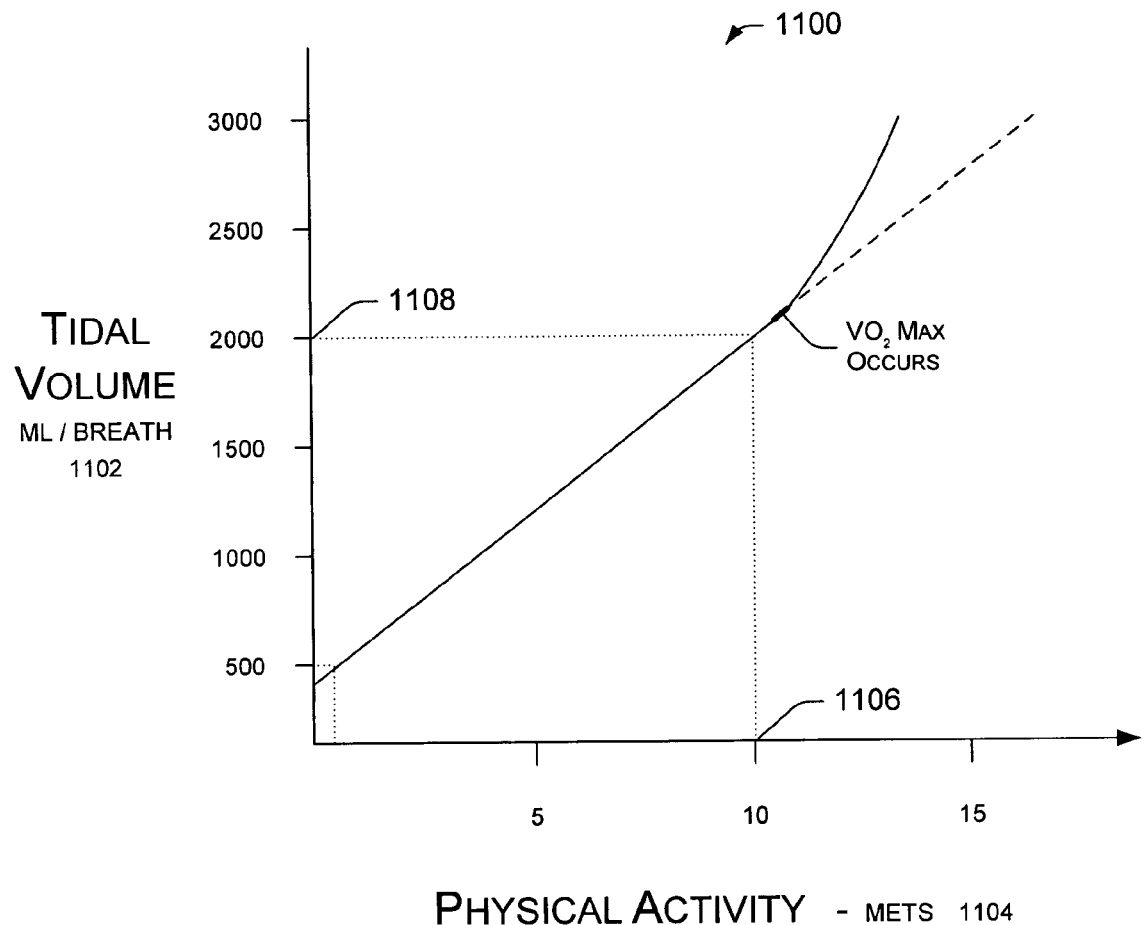
FIG. 11 is a graphical representation of an exemplary relationship for associating tidal volume with physical activity level.

FIG. 11 shows an exemplary relationship 1100 associating tidal volume 1102 to physical activity 1104 for use in selecting a target tidal volume when inducing respiration. The exemplary relationship 1100 adopts an exemplary nearly linear relationship between tidal volume 1102 and physical activity level 1104.

A metabolic equivalent, or "met," is a measure of physical activity 1104. One met is equivalent to $VO_2$ at rest, that is, approximately 3.5 ml of oxygen per kilogram bodyweight per minute, or in energy terms, one kilocalorie per kilogram of bodyweight per hour. For example, walking slowly occurs at a physical activity level of approximately two mets; walking at four miles per hour at a physical activity level of approximately five mets; jogging at six miles per hour occurs at a level of approximately eight mets; vigorous cycling at a level of approximately twelve mets; etc.

If the measured or predicted physical activity level is 10 mets, for example, the target tidal volume might be 2000 ml per breath, an increase of 1500 ml over the average resting tidal volume of 500 ml per breath (at a resting activity level requiring 1 met). Although the linearity of this exemplary relationship 1100 may break down above $VO_2$ max, when metabolic pathways become overwhelmingly aerobic, still the exemplary relationship 1100 can be useful for deriving target tidal volumes at various levels of physical activity before $VO_2$ max is reached.

Figure 12:
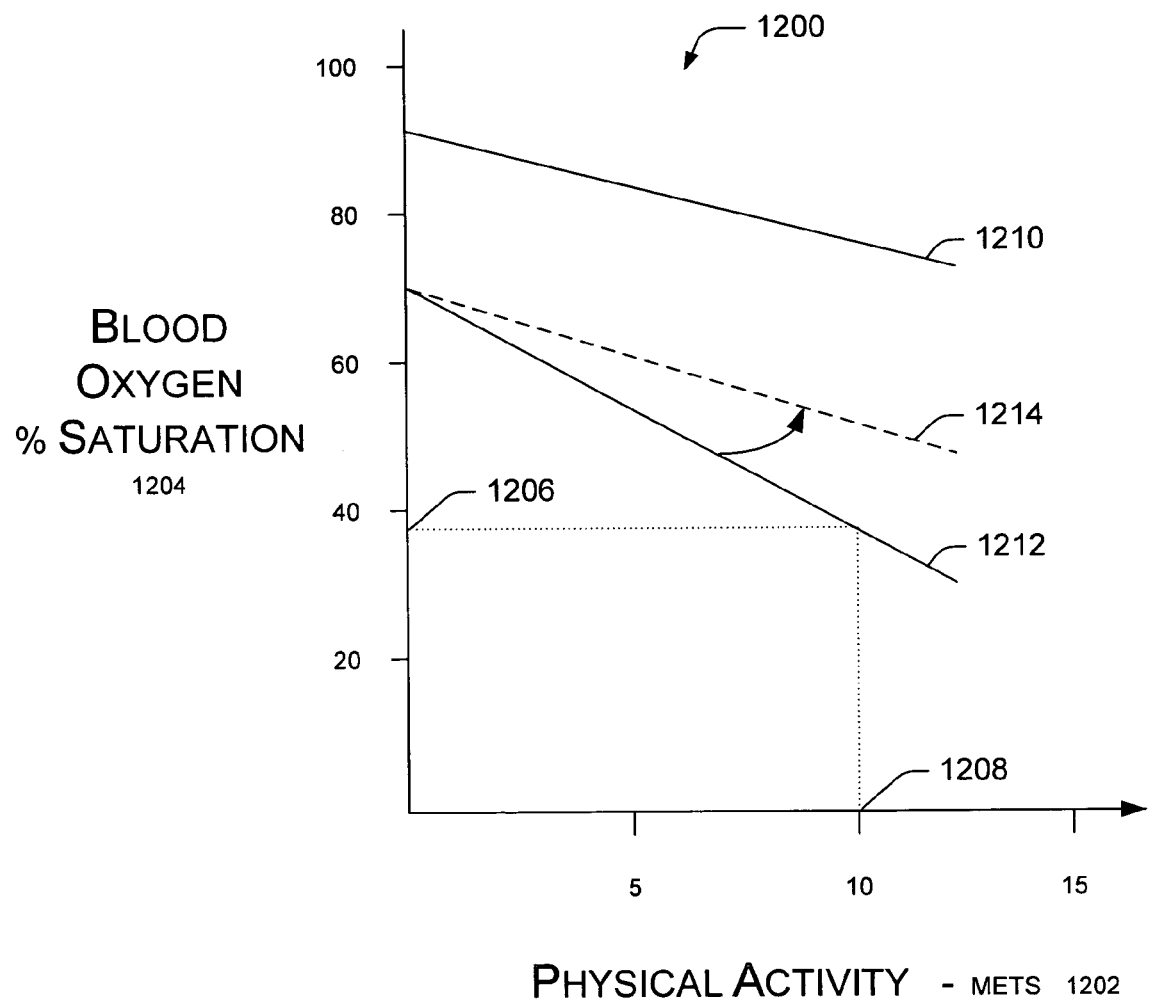
FIG. 12 is a graphical representation of an exemplary relationship for associating blood oxygen percentage saturation to physical activity level, for use in an exemplary method of FIG. 11.

FIG. 12 shows an exemplary relationship 1200 for associating a blood gas parameter, in this case the patient's blood oxygen percentage saturation level, to a patient's physical activity level. By measuring blood oxygen saturation levels using one or more blood chemistry sensor probes 140, the patient's physical activity level may be approximated. The physical activity level, in turn, can be used in the exemplary relationship 1100 shown in FIG. 11 to obtain a target tidal volume for the patient. It should be noted that this exemplary relationship 1200 may be most useful when a patient's blood oxygen response to physical activity is known and can be programmed into an exemplary device 100.

The total oxygen content of a patient's blood ($CaO_2$) is a combination of the amount of oxygen gas dissolved in the blood ($PaO_2$) and the oxygen saturation of hemoglobin in the blood ($SaO_2$), which in turn is a function of hemoglobin concentration in the blood (e.g., an anemic patient with low hemoglobin may still have full saturation of the hemoglobin). As physical activity and oxygen demand at the cellular level increase in some patients, the magnitude of blood oxygen desaturation is measurable and relatively predictable, especially in heart failure patients with compromised oxygen transport. This predictability allows, as shown in FIG. 12, blood oxygen percentage saturation levels 1204 to be plotted against physical activity 1202 in units of mets.

A first blood oxygen response to physical activity for a patient with a first degree of heart failure is illustrated by line 1210. Another blood oxygen response to physical activity in another patient with more severe heart failure is illustrated by line 1212. For this later patient, a severely decreased blood oxygen saturation, for example, 38%, corresponds to an increased physical activity requiring, for example, 10 mets of energy. Using the exemplary relationship 1100 shown in FIG. 11, the tidal volume associated with a 10 met activity level can be selected as the target tidal volume for inducing or performing respiration in the patient via an exemplary device 100. When the target tidal volume obtained via the exemplary relationship 1100 of FIG. 11 is applied by an exemplary device 100, the application of the target tidal volume aims to improve the patient's blood oxygen saturation to more normal values for the particular level of physical activity, for example, to a value on line 1214 instead of a value on line 1212.

An exemplary relationship 1200 between a physiological variable, such as blood oxygen saturation, and physical activity is presented to illustrate the importance of physical activity in predicting a target tidal volume value. Of course, another exemplary relationship could be set up directly between blood oxygen saturation and tidal volume, eliminating intervention of the physical activity variable. However, since other physiological variables, such as movement of a particular bodily part, cardiac contractility, etc., and other chemical variables, such as blood pH, blood carbon dioxide, etc., can be used in addition to or instead of one or more blood oxygen saturation levels to gauge a patient's physical activity level, such exemplary relationships that include the physical activity variable are useful. A value for each physiological variable can be associated with different levels of physical activity and used for obtaining a target tidal volume for stimulating respiration.

In one implementation, an exemplary device 100 measures a difference between an arterial blood oxygen saturation and a venous blood oxygen saturation to determine a patient's activity level. That is, the blood oxygen saturation differential is plotted against physical activity instead of a blood oxygen saturation percentage 1204. Thus, in this implementation, the difference between the amount of oxygen being supplied to active bodily muscle tissues versus the amount remaining on return of venous blood—i.e., the difference in arterial and venous blood oxygen saturations—gives an indication of the patient's physical activity level.

Figure 13:
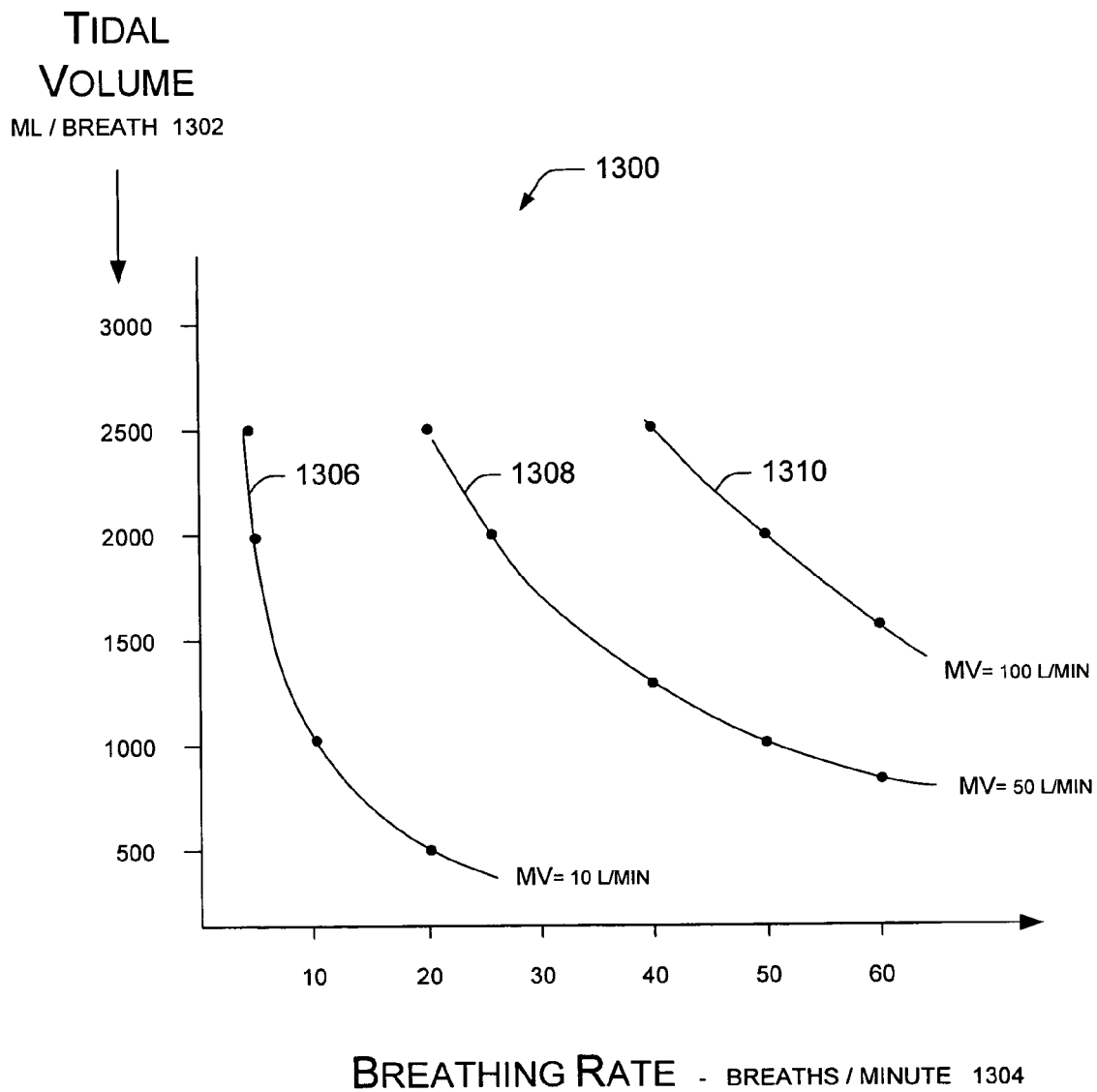
FIG. 13 is a graphical representation of an exemplary relationship for associating tidal volume with breathing rate.

FIG. 13 shows an exemplary relationship 1300 for associating a set of target tidal volumes 1302 to a set of breathing rates 1304 for use in obtaining a target tidal volume from a given breathing rate or vice-versa for stimulating respiration. In this exemplary relationship 1300, MV parametrics are used to create a stepped schema, that is, a few MV values are selected to relate tidal volume 1302 and breathing rate 1304 to each other along a limited number of isovolumetric curves. For example, in the illustrated exemplary relationship 1300, a 10 liter (per minute) isovolumetric curve 1306, a 50 liter isovolumetric curve 1308, and a 100 liter isovolumetric curve 1310 are illustrated.

In an exemplary method employing the exemplary relationship 1300, a particular selected MV value, for example 10 liters per minute, is maintained until the patient can benefit from the next higher or lower MV level, which is then adopted as the new target. Thus, for a measured or projected MV value of 10 liters per minute, the exemplary 10 liter per minute isovolumetric curve 1306 allows such combinations as breathing at 10 breaths per minute with a tidal volume of 1000 ml per breath, or breathing at 20 breaths per minute with a tidal volume of 500 ml per breath. A default combination, i.e., an ordered pair consisting of a breathing rate and a tidal volume, can be selected to initially implement each selected MV value, i.e., each isovolumetric curve. When switching from one MV value to the next allowed value, a device implementing the exemplary relationship 1300, such as exemplary device 100, can begin with the default combination. Alternatively, either the former breathing rate or the former tidal volume can be maintained when switching to the next MV level, and an exemplary device 100 changes the non-maintained variable so that when multiplied by the maintained variable the product of the two variables achieves the value of the next MV level.

The stepped approach just described is only one way to implement the subject matter of relating breathing rates to tidal volumes and MVs. The stepped approach, however, may save processing power in an implanted device when compared with other techniques that require more calculation or physiological sensing.

Figure 14:
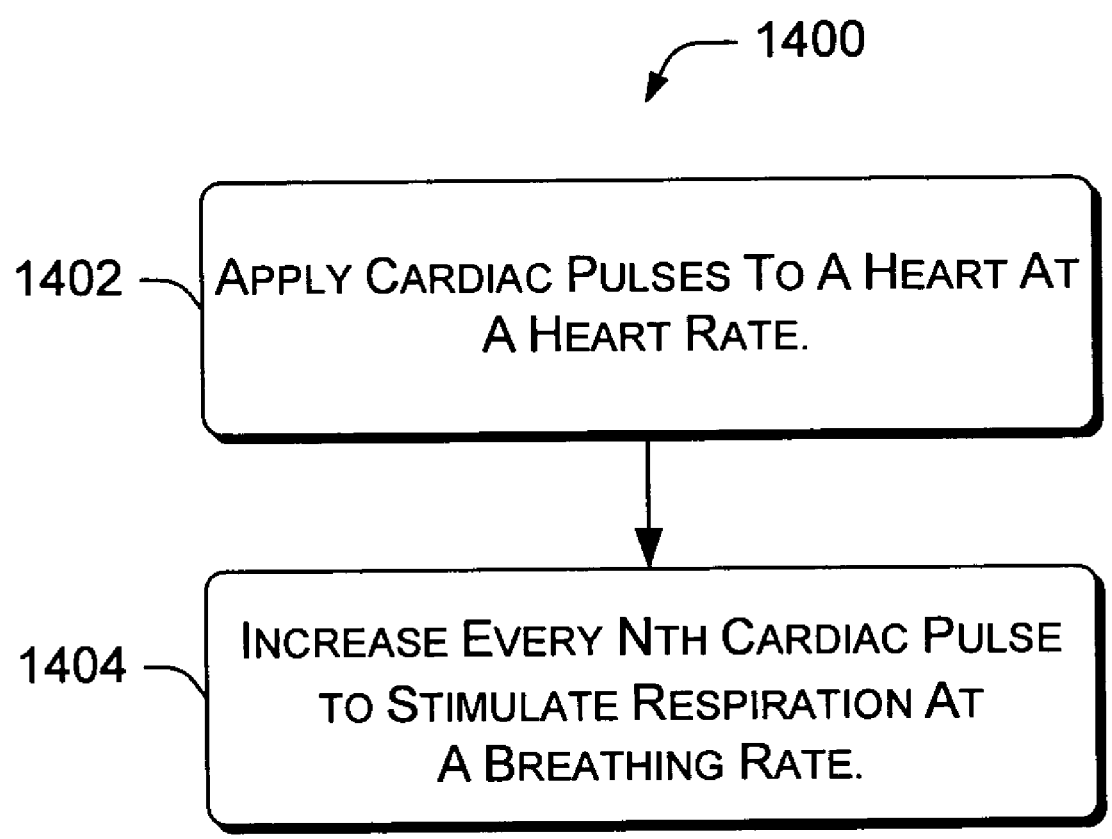
FIG. 14 is a flowchart of an exemplary method for delivering respiratory stimulation with cardiac pacing stimulation.

FIG. 14 shows an exemplary method 1400 for delivering target breathing rate stimulation to induce respiration in a patient. According to this exemplary method 1400, an implantable device, such as the exemplary device 100, is programmed to apply cardiac pacing pulses to treat a patient needing cardiac pacing therapy and to apply breathing rate stimulation, especially during episodes of sleep apnea or during exercise. Of course other devices could be used to practice the exemplary method 1400 besides the exemplary device 100. In the flow diagram, the operations are summarized in individual blocks. The operations may be performed in hardware and/or as machine-readable instructions (software or firmware) that can be executed by a device, such as an exemplary device 100 that includes a microcontroller 220.

At block 1402, cardiac pacing pulses are applied at a heart rate. The applied cardiac pacing pulses may perform atrial and ventricular (A-V) pacing, or may perform only ventricular pacing. The pacing pulses applied at the heart rate typically have enough amplitude to stimulate cardiac muscle, but not enough amplitude to induce respiration in the patient.

At block 1404, the amplitude of every Nth cardiac pacing pulse is increased to stimulate respiration at the target breathing rate in addition to stimulating the heart at the cardiac pacing rate. Pulses to be delivered at the target breathing rate are synchronized with some of the pulses being delivered for cardiac pacing to form an application pattern wherein every Nth pulse has the dual function of stimulating both the heart rate and respiration. The increased amplitude of an Nth pacing pulse is high enough to induce respiration, i.e., to at least initiate a respiration cycle.

Figure 15:
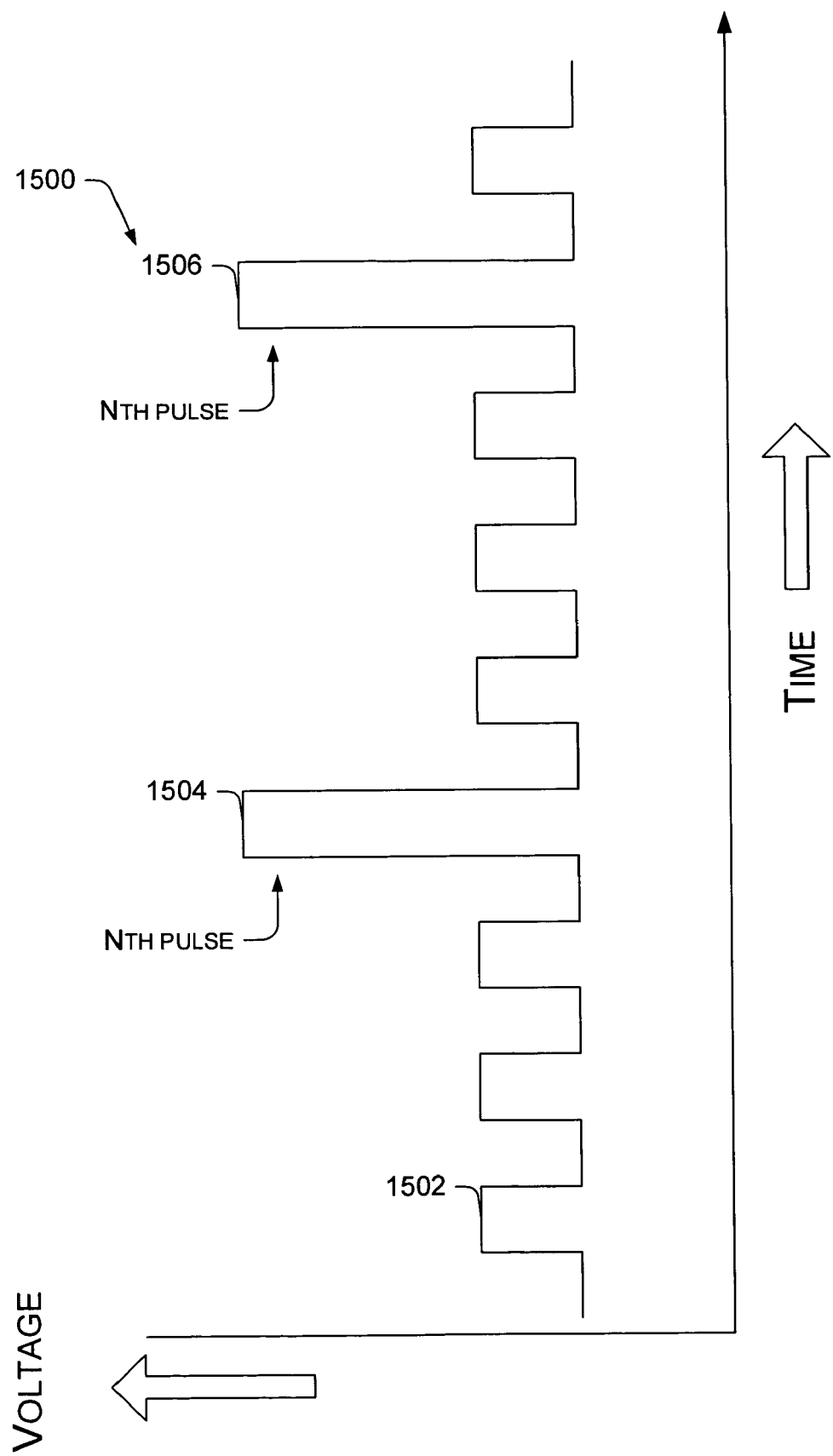
FIG. 15 is a diagrammatic illustration of an exemplary application pattern for stimulation delivered using the exemplary method of FIG. 14.

FIG. 15 shows an exemplary application pattern 1500 of pacing pulses in which every Nth pulse provides both cardiac and respiratory stimulation, for example, in a ratio of four heart beats per one induced respiration. The pulses of lower amplitude, e.g., 1502, stimulate only the heart while pulses of higher amplitude, i.e., the Nth pulses 1504 and 1506, stimulate both the heart and induce respiration, e.g., by stimulating the nearby phrenic nerve. If the heart rate and/or another target breathing parameter to be applied change, then the application pattern is recalibrated using a new heart beat to respiration ratio.

The exemplary application pattern 1500 may be used effectively via a coronary sinus lead 106 for stimulating both the heart muscles for cardiac pacing and the phrenic nerve innervating the diaphragm muscle. The exemplary application pattern 1500 can also be used in such a way that both the low amplitude pulses 1502 and the higher amplitude pulses 1504, 1506 are applied via one or more leads to the heart while only the higher amplitude pulses 1504 and 1506 are applied by a different lead to the phrenic nerve or to an electrode to directly stimulate the diaphragm muscle, e.g., in patient's that have a nonfunctional phrenic nerve.

Figure 16:
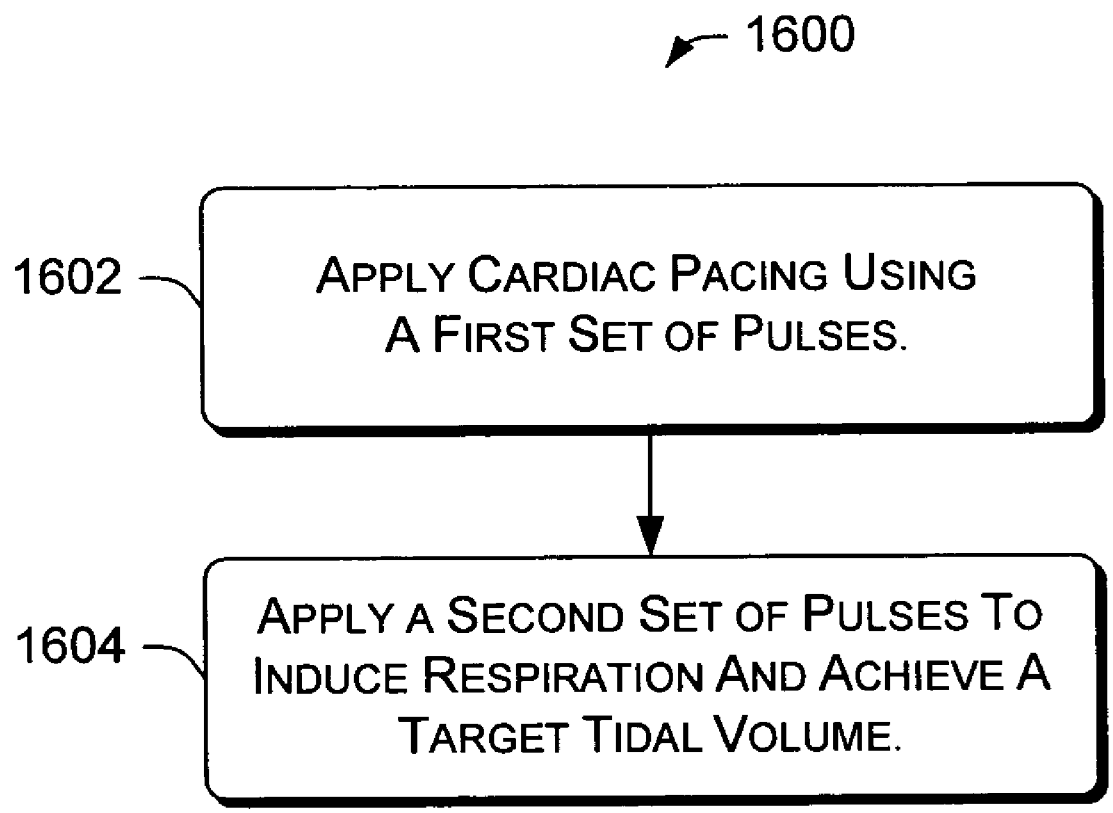
FIG. 16 is a flowchart of an exemplary method for delivering cardiac stimulation using a first set of pulses and tidal volume stimulation using a second set of pulses.

FIG. 16 shows an exemplary method 1600 for delivering electrical pulses to achieve a target tidal volume. According to this method, an implantable device, such as the exemplary device 100, is programmed to apply cardiac pacing pulses and to apply respiratory stimulation, especially during episodes of sleep apnea or during exercise. Of course other devices could be used to practice the exemplary method 1600 besides the exemplary device 100.

In the flow diagram, the operations are summarized in individual blocks. The operations may be performed in hardware and/or as machine-readable instructions (software or firmware) that can be executed by a device, such as an exemplary device 100 that includes a microcontroller 220.

At block 1602, cardiac pacing pulses, if any are currently needed, are applied with a first set of electrical impulses. The applied pacing pulses may perform atrial and ventricular (A-V) pacing, or may perform only ventricular pacing. Alternatively, no cardiac pacing pulses may be currently applied. If cardiac pacing pulses are applied, the pacing pulses typically have enough amplitude to stimulate cardiac muscle, but not enough amplitude to induce respiration.

At block 1604, a second set of electrical pulses are applied to achieve the target tidal volume. Alternatively, the second set of pulses may be applied using the same lead that applies the first set of cardiac pacing pulses, if the lead is in a position to stimulate both cardiac pacing and respiration. The second set of pulses can also be delivered using a lead that is separate from the lead that delivers the set of cardiac pacing pulses.

Figure 17:
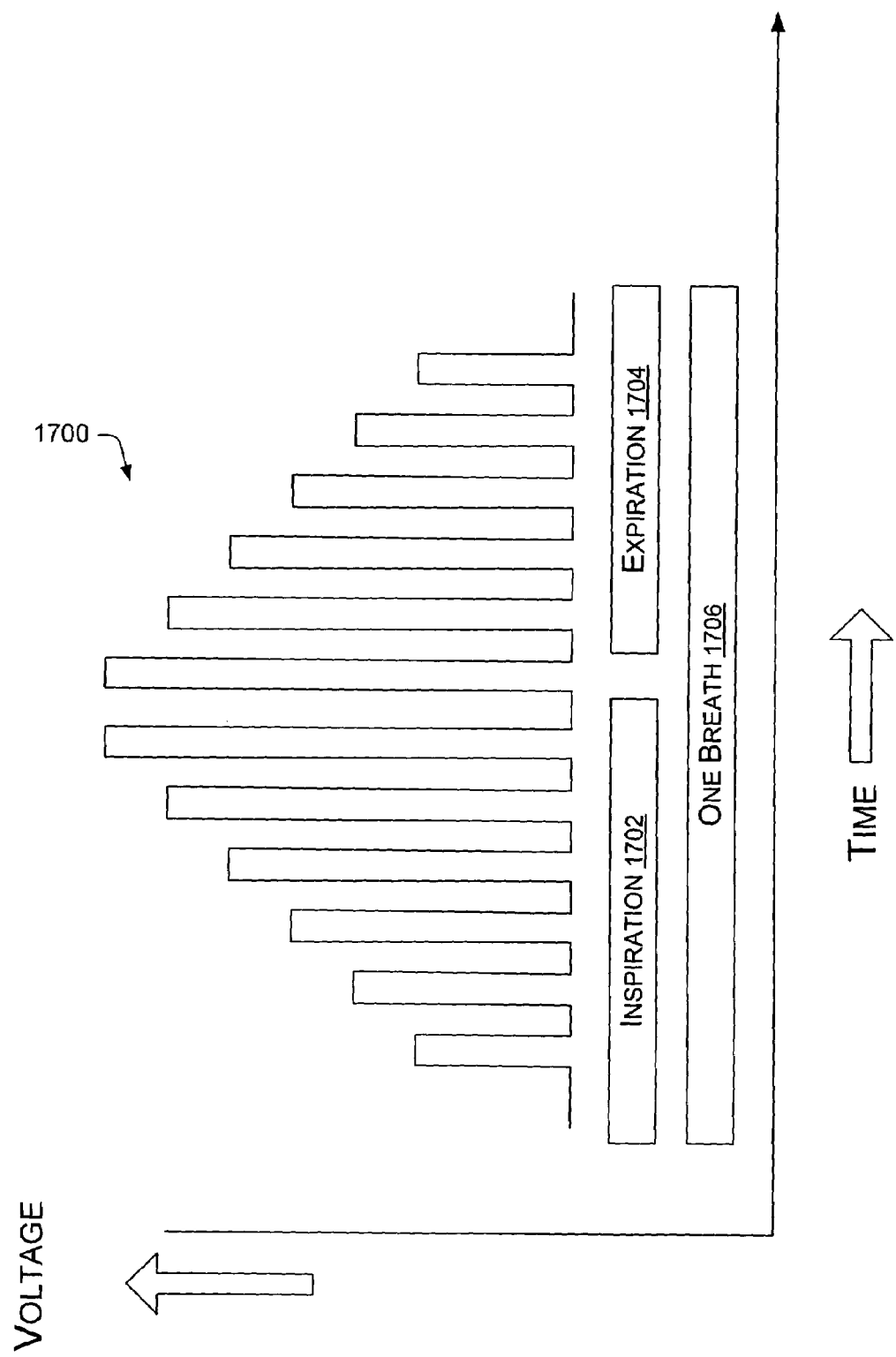
FIG. 17 is a diagrammatic illustration of exemplary pulse waveforms for delivering tidal volume stimulation for respiration.

FIG. 17 shows an exemplary application pattern 1700 of electrical pulses for achieving a target tidal volume during a patient's respiration cycle. A series of pulses are delivered in order of ascending amplitude to progressively contract the diaphragm muscle to effect inspiration 1702. Upon achieving the target tidal volume a series of pulses are delivered in order of descending amplitude to progressively release the diaphragm muscle to effect expiration 1704. The series of pulses creating inspiration 1702 and the series of pulses creating expiration 1704 represent one respiratory cycle 1706, that is, one patient breath.

Alternatively, the diaphragm muscle and thus the lungs may be allowed to relax and deflate of their own accord without a need for the series of pulses in a descending amplitude order.

CONCLUSION

The foregoing discussion describes exemplary devices, relationships, and methods for obtaining target respiratory parameters from heart rate information and in some cases from various physiological and metabolic information. The target respiratory parameters may be delivered by an implantable device to a patient during periods of altered respiration, such as sleep apnea or exercise. Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A method, comprising:
   delivering cardiac stimulation pulses to a patient's heart at a heart rate;
   obtaining heart rate information for the patient;
   obtaining a sensed respiratory parameter for the patient;
   determining a target respiratory parameter based at least in part on the heart rate information;
   comparing the sensed respiratory parameter to the target respiratory parameter; and
   delivering respiratory stimulation if the target respiratory parameter is greater than the sensed respiratory parameter, wherein the delivery of respiratory stimulation is synchronized with the delivery of cardiac stimulation pulses so as to affect respiratory function of the patient without affecting the heart rate, except for every Nth cardiac stimulation pulse, wherein the amplitude of the cardiac pacing stimulation pulse is increased to an energy level sufficient to both stimulate the heart and induce respiration.

2. The method as recited in claim 1, wherein the sensed and target respiratory parameters comprise a breathing rate.

3. The method as recited in claim 2, wherein the target breathing rate is obtained by multiplying a heart rate by a cardiac stroke volume to obtain a cardiac output value, relating the cardiac output value to a respiratory ventilation rate, and dividing the respiratory ventilation rate by a volume of at least part of the patient's lungs.

4. The method as recited in claim 1, wherein the target respiratory parameter comprises a target tidal volume based at least in part on the heart rate information.

5. The method as recited in claim 4, further comprising obtaining the target tidal volume based at least in part on a breathing rate parameter.

6. A device comprising:
   means for delivering cardiac stimulation pulses to a patient's heart at a heart rate;
   means for obtaining heart rate information associated with the patient;
   means for obtaining a native respiratory parameter for the patient;
   means for determining a target respiratory parameter based at least in part on the heart rate information;
   means for comparing the native respiratory parameter to the target respiratory parameter; and
   means for delivering respiratory stimulation if the target respiratory parameter is greater than the native respiratory parameter, wherein the delivery of respiratory stimulation is synchronized with the delivery of cardiac stimulation pulses so as to affect respiratory function of the patient without affecting the heart, except for every Nth cardiac stimulation pulse, wherein the amplitude of the cardiac pacing stimulation pulse is increased to an energy level sufficient to both stimulate the heart and induce respiration.

7. The device as recited in claim 6, wherein the native and target respiratory parameters comprise a breathing rate, and means for determining a target respiratory parameter comprise means for squaring a heart rate and dividing the squared heart rate by 360.

8. The device as recited in claim 6, wherein the native and target respiratory parameters comprise a breathing rate, and means for determining a target respiratory parameter comprise means for dividing the heart rate by an integer.

9. The device as recited in claim 6, wherein the native and target respiratory parameters comprise a breathing rate and means for determining a target respiratory parameter comprises:
   means for multiplying a heart rate by a cardiac stroke volume to obtain a cardiac output value;
   means for relating the cardiac output value to a respiratory ventilation rate; and
   means for dividing the respiratory ventilation rate by a volume of at least part of the patient's lungs.

10. The device as recited in claim 6, wherein means for delivering or not delivering respiratory stimulation based on the comparison comprises:
    means for applying electrical pulses to stimulate respiration if the target respiratory parameter is greater than the native respiratory parameter; and
    means for inhibiting delivery of the electrical pulses if the target respiratory parameter is less than the native respiratory parameter.

11. The device as recited in claim 6, wherein the native and target respiratory parameters comprise a tidal volume, and means for determining a target respiratory parameter comprise means for correlating heart rate information with target tidal volumes.

12. The device as recited in claim 6, wherein the native and target respiratory parameters comprise a tidal volume, and means for determining a target respiratory parameter comprise means for correlating physical activity with target tidal volumes.

13. The device as recited in claim 6, wherein the native and target respiratory parameters comprise a tidal volume, and means for determining a target respiratory parameter comprise means for correlating breathing rate with target tidal volumes.

14. The device as recited in claim 8, wherein the integer is different for different heart rate ranges.

15. A method, comprising:
    delivering cardiac stimulation pulses to a patient's heart at a heart rate;
    obtaining heart rate information for the patient;
    obtaining a sensed respiratory parameter for the patient;
    determining a target respiratory parameter based at least in part on the heart rate information;
    comparing the sensed respiratory parameter to the target respiratory parameter; and
    delivering respiratory stimulation if the target respiratory parameter is greater than the sensed respiratory parameter, wherein the delivery of respiratory stimulation is synchronized with the delivery of cardiac stimulation pulses so as to affect respiratory function of the patient without affecting the heart rate, wherein delivering respiratory stimulation further comprises increasing a series of cardiac stimulation pulses in order of ascending amplitude to progressively contract the diaphragm to effect inspiration.

16. The method of claim 15 further comprising, after inspiration, decreasing a series of cardiac stimulation pulses in order of descending amplitude to progressively release the diaphragm to effect expiration.

* * * * *